(12) United States Patent
Furukawa et al.

(10) Patent No.: US 10,959,925 B2
(45) Date of Patent: *Mar. 30, 2021

(54) HAIR COSMETIC COMPOSITION

(71) Applicant: KAO CORPORATION, Tokyo (JP)

(72) Inventors: Jun-ichi Furukawa, Tokyo (JP); Shinichi Tokunaga, Tokyo (JP); Steven Breakspear, Darmstadt (DE); Niu Jian, Darmstadt (DE); Bernd Noecker, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/306,542

(22) PCT Filed: Jun. 2, 2017

(86) PCT No.: PCT/EP2017/063525
§ 371 (c)(1),
(2) Date: Nov. 30, 2018

(87) PCT Pub. No.: WO2017/207786
PCT Pub. Date: Dec. 7, 2017

(65) Prior Publication Data
US 2019/0254943 A1    Aug. 22, 2019

(30) Foreign Application Priority Data
Jun. 3, 2016 (JP) .............................. JP2016-112266

(51) Int. Cl.
| A61K 8/19 | (2006.01) |
| A61K 8/34 | (2006.01) |
| A61K 8/36 | (2006.01) |
| A61K 8/39 | (2006.01) |
| A61K 8/49 | (2006.01) |
| A61Q 5/04 | (2006.01) |
| A61Q 5/06 | (2006.01) |

(52) U.S. Cl.
CPC ............... *A61K 8/347* (2013.01); *A61K 8/19* (2013.01); *A61K 8/34* (2013.01); *A61K 8/345* (2013.01); *A61K 8/36* (2013.01); *A61K 8/39* (2013.01); *A61K 8/498* (2013.01); *A61Q 5/04* (2013.01); *A61Q 5/06* (2013.01); *A61K 2800/5922* (2013.01); *A61K 2800/88* (2013.01); *A61K 2800/882* (2013.01); *A61K 2800/884* (2013.01)

(58) Field of Classification Search
CPC ....................................................... A61K 8/19
See application file for complete search history.

(56) References Cited

U.S. PATENT DOCUMENTS 4,278,659 A    7/1981    Breuer

FOREIGN PATENT DOCUMENTS

| EP | 1880706 A1 | 1/2008 |
| EP | 2538916 A2 | 1/2013 |
| EP | 3 225 229 A | 10/2017 |
| EP | 3 228 300 A | 10/2017 |
| EP | 3 228 302 A | 10/2017 |
| EP | 3 228 303 A | 10/2017 |
| JP | 2009-537619 A | 10/2009 |
| JP | 2015-120660 A | 7/2015 |
| WO | WO-2007/135298 A1 | 11/2007 |
| WO | WO-2009/035970 A1 | 3/2009 |
| WO | WO-2011/104282 A2 | 9/2011 |
| WO | WO-2014/068102 A2 | 5/2014 |
| WO | WO-2014/131469 A1 | 9/2014 |
| WO | WO-2015/095671 A1 | 6/2015 |
| WO | WO-2017/041904 A | 3/2017 |

OTHER PUBLICATIONS

"Glyoxylic Acid," Wikipedia, dated May 8, 2013, XP055085717, retrieved from the Internet on Oct. 29, 2013.
International Search Report and Written Opinion issued in International Application No. PCT/EP2017/063525 dated Jul. 31, 2017.
Wong et al., "Mechanism of Hair Straightening," Journal of the Society of Cosmetic Chemist, vol. 45, pp. 347-352, Nov./Dec. 1994.

*Primary Examiner* — Benjamin J Packard
(74) *Attorney, Agent, or Firm* — Foley & Lardner LLP

(57) ABSTRACT

The hair cosmetic composition of the present invention, which is a one-agent type or a multi-agent type hair cosmetic composition, contains, the following components (A) to (D), the component (C) content, relative to the total composition of the hair cosmetic composition, being 0.1 mass % or higher and lower than 20 mass %:
(A): a compound selected from the group consisting of glyoxylic acid, a glyoxylic acid hydrate, a glyoxylate salt, and a glyoxylamide;
(B): a phenolic compound having an electron-donating group on at least one m-position and having a hydrogen atom on at least one of the o-positions and the p-position, wherein the electron-donating group on the m-position may form, together with an adjacent carbon atom, a benzene ring optionally substituted with hydroxyl group(s);
(C): an organic solvent having a boiling point of 100° C. or higher; and
(D): water.

25 Claims, No Drawings

HAIR COSMETIC COMPOSITION

RELATED APPLICATIONS

The present application claims priority under 37 U.S.C. § 371 to International Patent Application No. PCT/EP2017/063525, filed Jun. 2, 2017, which claims priority to and the benefit of Japanese Patent Application No. 2016-112266, filed on Jun. 3, 2016. The contents of these applications are hereby incorporated by reference in their entireties.

FIELD OF THE INVENTION

The present invention relates to a hair cosmetic composition which can shape hair semi-permanently or permanently.

BACKGROUND OF THE INVENTION

Conventionally, semi-permanent or permanent deforming of hair is carried out through a technique such as using a reducing agent (e.g., permanent waving) or using a strong alkaline hair treatment agent (pH: 12 to 14), typically an alkaline relaxer. These techniques, however, are well known to considerably damage hair for a long period of time. In recent years, there has been developed a curly or frizzy hair straightening method employing a large amount of formaldehyde, as a method for semi-permanently or permanently deforming hair with less hair damage. However, the method, employing highly toxic formaldehyde, must be performed with care due to the high volatility of formaldehyde. Thus, the method is not a preferred hair treatment method.

For overcoming these drawbacks, there have been investigated such treatment methods which do not damage hair, which employ no formaldehyde, and which is more safe to the human body. For example, Patent Document 1 discloses a technique for straightening strongly curled hair, which technique includes applying an α-keto acid, particularly glyoxylic acid, and heating the hair at 200° C.±50° C. by means of a flat iron. Patent Document 2 discloses a method of continuously relaxing keratin fiber, the method including applying a polyhydroxyl aromatic compound to hair and heating the hair at 110° C. or higher.

Meanwhile, temporary hair deforming, in which the shaped hair can be freed by rinsing with water, is realized by use of a shaping agent. For example, Patent Document 3 discloses a hair use composition containing an oligomer produced through heat reflux of glyceraldehyde and resorcin in the presence of boric acid or silicic acid. The composition enhances hair set retention performance and moisture resistance. When the user wets the hair, new shaping of the hair can be performed. In addition, mechanical strength of the hair can be enhanced.

Patent Document 1: EP-A-2538916
Patent Document 2: JP-A-2009-537619
Patent Document 3: U.S. Pat. No. 4,278,659

SUMMARY OF THE INVENTION

The present invention provides a hair cosmetic composition, which is a one-agent type hair cosmetic composition composed of a single agent, or a multi-agent type hair cosmetic composition composed of multiple agents, wherein the hair cosmetic composition totally comprising the following components (A) to (D), the component (C) content, relative to the total composition of the hair cosmetic composition, being 0.1 mass % or higher and lower than 20 mass %:

(A): one or more species selected from the group consisting of glyoxylic acid, a glyoxylic acid hydrate, a glyoxylate salt, and a glyoxylamide;

(B): a phenolic compound having an electron-donating group on at least one m-position and having a hydrogen atom on at least one of the o-positions and the p-position, wherein the electron-donating group on the m-position may form, together with an adjacent carbon atom, a benzene ring optionally substituted with hydroxyl group(s);

(C): an organic solvent having a boiling point of 100° C. or higher at 1,013.25 hPa; and (D): water.

The present invention further provides a method for the treatment of hair, realizing semi-permanent or permanent deforming of hair, the method comprising the following steps (i) and (ii);

(i) a step of applying the hair cosmetic composition to hair; and (ii) a step of heating and shaping the hair to which the hair cosmetic composition is applied.

DETAILED DESCRIPTION OF THE INVENTION

When hair treatment is performed by use of any hair treatment agent as employed in the methods disclosed in Patent Document 1 or 2, the hair cannot be waved or curled semi-permanently or permanently, and semi-permanent straightening is possible. Also, when the user wishes to change the semi-permanently or permanently straightened hair to a new hair shape (e.g., wavy or curly) semi-permanently or permanently, a conventionally performed treatment employing a reducing agent is required. This conventional technique is very cumbersome and time-consuming, and the treated hair is damaged.

The technique disclosed in Patent Document 3 employs an oligomer as a hair treatment agent, which can be washed off with water. Thus, the set hair shape is restored by repeated shampooing processes. In this sense, the hair deforming is not defined as semi-permanent or permanent deforming.

The present inventors previously conceived that hair can be straightened or provided with any shape such as curly or wavy semi-permanently, by applying a hair cosmetic composition containing glyoxylic acid and a specific phenolic compound and heating the hair. However, it was found that the hair treated by this hair treatment agent has an increased stiffness which results in stiff touch feeling.

In view of the foregoing, the present invention is directed to a hair cosmetic composition, which is safe to the human body and causes less damage to hair; which can semi-permanently or permanently straighten hair or impart a wavy shape or a curly shape to hair; which can semi-permanently or permanently change the shaped hair shape to another hair shape in a simple way without using a hair cosmetic composition such as a reducing agent and giving no damage to the hair; and which can impart soft touch feeling to the treated hair.

The present inventors have found the following. Specifically, a hair cosmetic composition containing glyoxylic acid and a specific phenolic compound can semi-permanently straighten hair or impart a curly shape of a wavy shape to the hair; and can change the hair shape to any shape different therefrom only by means of heating means such as a hair iron or a curler without performing a treatment by use of a hair treatment agent such as a reducing agent, when the hair has been treated with the hair treatment of the hair cosmetic composition. Furthermore, through addition of a specific amount of a non-volatile organic solvent, soft touch feeling can be imparted to the treated hair without impairing the above-mentioned effect for deforming the shape of hair. The present invention has been accomplished on the basis of these findings.

As used herein, the expression "deforming of hair semi-permanently or permanently" refers to the shape of hair being maintained after repeated shampooing processes (i.e., with excellent shampooing resistance). More specifically, the expression and an equivalent expression refer to, when the deformed hair is washed with a shampoo, sufficiently rinsed off with water, and naturally dried, the shape of the hair is unchanged before and after shampooing. Notably, the expression "the shape of hair is not changed" refers to no substantial change in the number of waves of wavy hair before and after shampooing, or no substantial generation of wavy hair or curled hair after shampooing straight hair.

As used herein, the term "deforming of hair (or hair deforming)" refers to a change in shape of a hair shaft via no scission or recombination of S—S bonds of a hair-component protein, and includes a change from straight hair to curly hair or the like, and a change from wavy hair, curly hair, or the like as well as naturally frizzy hair or the like to straight hair.

The hair cosmetic composition of the present invention encompasses a one-agent type hair cosmetic composition composed of a single agent, and a multi-agent type hair cosmetic composition composed of multiple agents (e.g., a 2-agent hair cosmetic composition). The multi-agent type hair cosmetic composition is categorized into a single-application composition, which is applied to hair after mixing a first agent, a second agent, and other components, and a successive-application composition, whose first agent, second agent, and the like is successively applied to hair.

As used herein, the term "the total hair cosmetic composition" refers to, in the case of a one-agent type hair cosmetic composition, the single agent forming the one-agent type hair cosmetic composition, and in the case of a single application multi-agent type hair cosmetic composition, a mixture containing all the compositions forming the multi-agent type hair cosmetic composition, at such compositional proportions that fall within the scope of the present invention, with the compositions being mixed before application of hair. In the case of a successive application multi-agent type hair cosmetic composition, which is not an actual mixture before application, "the total hair cosmetic composition" refers to a conceptual mixture containing all the compositions forming the multi-agent type hair cosmetic composition, at such compositional proportions that fall within the scope of the present invention.

[Component (A): Glyoxylic Acid, Glyoxylic Acid Hydrate, Glyoxylate Salt, or a Glyoxylamide]

Component (A) includes any of glyoxylic acid, a glyoxylic acid hydrate, a glyoxylate salt, and a glyoxylamide. Examples of the glyoxylic acid hydrate include glyoxylic acid monohydrate. Examples of the glyoxylate salt include an alkali metal glyoxylate and an alkaline earth metal glyoxylate. Examples of the alkali metal include lithium, sodium, and potassium, and examples of the alkaline earth metal include magnesium and calcium. Examples of the glyoxylamide include N-glyoxyloylcarbocysteine and N-glyoxyloylkeratinamino acid.

From the viewpoints of enhancing a effect for deforming the shape of hair of the hair cosmetic composition of the present invention, further enhancing resistance of the hair shape against shampooing, further enhancing the re-deforming effect of the hair which has been semi-permanently deformed via heating, and further enhancing the resistance to shampooing after re-deforming of the hair, the hair cosmetic composition of the present invention preferably has a component (A) content, relative to the total composition of the hair cosmetic composition and in terms of glyoxylic acid, of 1 mass % or higher, more preferably 2.0 mass % or higher, still more preferably 2.5 mass % or higher, yet more preferably 3.0 mass % or higher. In addition to the aforementioned viewpoints, from a further viewpoint of suppressing irritation to the skin, the component (A) content is preferably 30 mass % or lower, more preferably 25 mass % or lower, still more preferably 20 mass % or lower, yet more preferably 15 mass % or lower, further more preferably 12 mass % or lower.

[Component (B): Phenolic Compound Having a Specific Structure]

Component (B) is a phenolic compound having an electron-donating group on at least one m-position (preferably on two m-positions) and having a hydrogen atom on at least one of the o-positions and the p-position. The electron-donating group on the m-position may form, together with an adjacent carbon atom, a benzene ring which may be further substituted with hydroxyl group(s). From the viewpoint of permeability to hair, the molecular weight of component (B) is preferably 100 or higher, more preferably 110 or higher, and 1,000 or lower, more preferably 700 or lower, still more preferably 500 or lower. Examples of the phenolic compound of component (B) include the following components (B1), (B2), and (B3):

(B1) resorcin;
(B2) a compound represented by formula (1); and
(B3) a compound represented by formula (2).

Component (B1) is a resorcin, represented by the following formula.

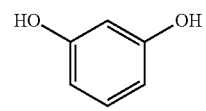

Component (B2) is a compound represented by formula (1):

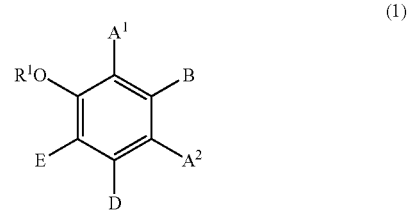

wherein:

$R^1$ represents a hydrogen atom or a methyl group;

$A^1$ and $A^2$, which may be identical to or different from each other, each represent a hydrogen atom, a C1 to C12 linear-chain or branched-chain alkyl or alkenyl group, an optionally substituted C7 to C12 aralkyl or arylalkenyl group, a C1 to C6 linear-chain or branched-chain alkoxy or alkenyloxy group, a halogen atom, or —CO—R² (wherein R² represents a C1 to C12 linear-chain or branched-chain alkyl or alkenyl group, an optionally substituted C7 to C12 aralkyl or arylalkenyl group, or an optionally substituted C6 to C12 aromatic hydrocarbon group);

B represents a hydrogen atom, a C1 to C12 linear-chain or branched-chain alkyl or alkenyl group, an optionally substituted C7 to C12 aralkyl or arylalkenyl group, or —OR³ or —COOR³ (wherein R³ represents a hydrogen atom or a C1 to C6 linear-chain or branched-chain alkyl or alkenyl group);

D represents a hydrogen atom, a hydroxyl group, a methyl group, or a C1 to C12 linear-chain or branched-chain alkoxy or alkenyloxy group; and E represents a hydrogen atom, a hydroxyl group, a C1 to C6 linear-chain or branched-chain alkyl or alkenyl group, or a C1 to C6 linear-chain or branched-chain alkoxy or alkenyloxy group, wherein two or three of $A^1$, $A^2$, B, and E each are a hydrogen atom, with each of remaining being a group which is not a sulfo group, and in the case where D is a hydrogen atom or a methyl group, $A^1$ and B, or $A^2$ and B form an optionally hydroxyl group-substituted benzene ring with two adjacent carbon atoms.

In the case where the aralkyl group, the arylalkenyl group, or the aromatic hydrocarbon group in represented by formula (1) have a substituent, examples of the substituent include a hydroxyl group, a C1 to C6 linear-chain or branched-chain alkyl or alkenyl group, and a C1 to C12 alkoxy group. The number of carbon atoms (Cn) of the aralkyl group, the arylalkenyl group, or the aromatic hydrocarbon group refers to the total number of the carbon atoms including those forming the substituents.

Examples of the C1 to C6 linear-chain or branched-chain alkyl or alkenyl group of $R^3$ or E include methyl, ethyl, n-propyl, isopropyl, n-butyl, isobutyl, sec-butyl, tert-butyl, n-pentyl, isopentyl, neopentyl, 1-methylpentyl, n-hexyl, isohexyl, vinyl, allyl, butenyl, and hexenyl.

Examples of the C1 to C6 linear-chain or branched-chain alkoxy or alkenyloxy group of $A^1$, $A^2$, or E include groups in which the aforementioned C1 to C6 alkyl or alkenyl group to which an oxygen atom is bonded.

Examples of the C1 to C12 linear-chain or branched-chain alkyl or alkenyl group in $A^1$, $A^2$, $R^2$, and B include the aforementioned C1 to C6 alkyl or alkenyl groups, n-heptyl, 2,4-dimethylpentyl, 1-n-propylbutyl, n-octyl, 2-ethylhexyl, n-nonyl, 1-methylnonyl, n-decyl, 3,7-dimethyloctyl, 2-isopropyl-5-methylhexyl, n-undecyl, n-dodecyl, and decenyl.

Examples of the C1 to C12 linear-chain or branched-chain alkoxy or alkenyloxy group of D include groups formed of the aforementioned C1 to C12 alkyl or alkenyl group to which an oxygen atom is bound.

Examples of the optionally substituted C7 to C12 aralkyl or arylalkenyl group of $A^1$, $A^2$, $R^2$, and B include benzyl, hydroxybenzyl, dihydroxybenzyl, phenylethyl, phenylethenyl, hydroxyphenylethyl, dihydroxyphenylethyl, hydroxyphenylethenyl, dihydroxyphenylethenyl, phenylpropyl, phenylpropenyl, phenylbutyl, phenylbutenyl, phenylpentyl, phenylpentenyl, phenylhexyl, and phenylhexenyl.

Examples of the optionally substituted C6 to C12 aromatic hydrocarbon group of $R^2$ include phenyl, hydroxyphenyl, dihydroxyphenyl, trihydroxyphenyl, naphthyl, hydroxynaphthyl, and dihydroxynaphthyl.

Examples of the halogen atom of $A^1$ and $A^2$ include fluorine, chlorine, and bromine.

Specific examples of the compound represented by formula (1) include a resorcin derivative represented by formula (1-1), a benzophenone derivative represented by formula (1-2), and a naphthol derivative represented by formula (1-3-a) or (1-3-b), which are shown in the following.

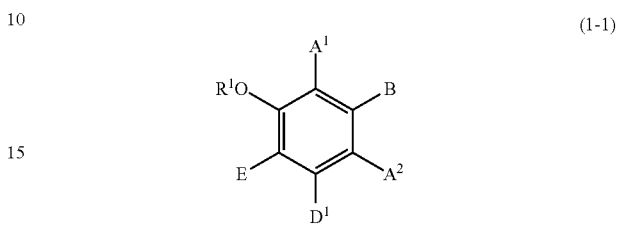

(1-1)

wherein $R^1$, $A^1$, $A^2$, B, and E are defined as above, and $D^1$ represents a hydroxyl group or a methoxy group

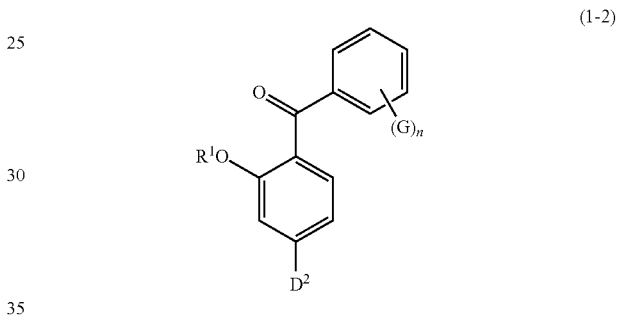

(1-2)

wherein $R^1$ has the same meaning as defined above; $D^2$ represents a hydroxyl group or a C1 to C12 alkoxy group; G represents a hydroxyl group, a C1 to C6 linear-chain or branched-chain alkyl or alkenyl group, or a C1 to C6 alkoxy group; and n is an integer of 0 to 2]

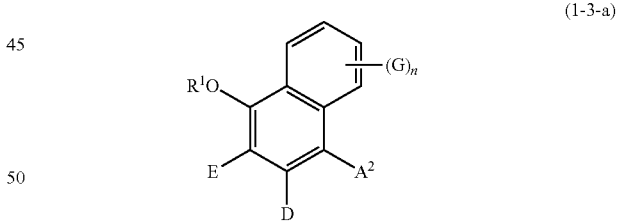

(1-3-a)

wherein $R^1$, $A^2$, E, D, G, and n are defined as above

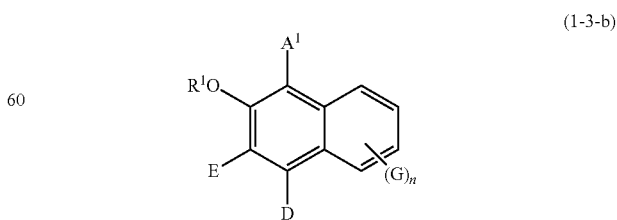

(1-3-b)

wherein $R^1$, $A^1$, E, D, G, and n are defined as above.

The compound represented by formula (1-1) is preferably any of the compounds (1-1-1) to (1-1-3)
(1-1-1) m-Dimethoxybenzene Derivative Represented by the Following Formula (1-1-1)

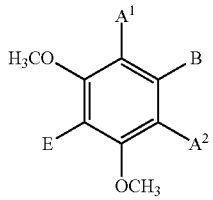

(1-1-1)

wherein $A^1$, $A^2$, B, and E are defined as above.

Each of $A^1$ and $A^2$ is preferably a hydrogen atom, a C1 to C4 linear-chain or a branched-chain alkyl or alkenyl group, more preferably a hydrogen atom.

B is preferably a hydrogen atom, a C1 to C4 alkyl or alkenyl group, an optionally substituted C7 to C10 arylalkenyl group, or a hydroxyl group, more preferably a hydrogen atom, an optionally substituted C7 to C10 arylalkenyl group, or a hydroxyl group.

E is preferably a hydrogen atom, a C1 to C4 linear-chain or branched-chain alkyl or alkenyl group, more preferably a hydrogen atom.

Examples of the compound (1-1-1) include 1,3-dimethoxybenzene, 3,5-dimethoxyphenol, 2,6-dimethoxyphenol, and 5-(hydroxyphenylethenyl)-1,3-dimethoxybenzene (trivial name: pterostilbene).

(1-1-2) m-Methoxyphenol Derivative Represented by the Following Formula (1-1-2)

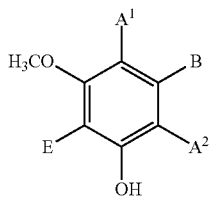

(1-1-2)

wherein $A^1$, $A^2$, B, and E are defined as above.

Each of $A^1$ and $A^2$ is preferably a hydrogen atom, a C1 to C12 linear-chain or branched-chain alkyl or alkenyl group, or an optionally substituted C7 to C12 aralkyl or arylalkenyl group, more preferably a hydrogen atom, a C1 to C6 linear-chain or branched-chain alkyl group, or an optionally substituted C7 to C10 arylalkenyl group.

B is preferably a hydrogen atom, a C1 to C12 linear-chain or branched-chain alkyl or alkenyl group, an optionally substituted C7 to C12 aralkyl or arylalkenyl group, or $-OR^3$ (wherein $R^3$ is a hydrogen atom or a C1 to C6 linear-chain or branched-chain alkyl or alkenyl group), more preferably a hydrogen atom, a C1 to C4 alkyl or alkenyl group, an optionally substituted C7 to C10 arylalkenyl group, or a hydroxyl group, still more preferably a hydrogen atom, an optionally substituted C7 to C10 arylalkenyl group, or a hydroxyl group.

E is preferably a hydrogen atom, a hydroxyl group, a C1 to C4 linear-chain or branched-chain alkyl or alkenyl group, or a C1 to C4 linear-chain or branched-chain alkoxy or alkenyloxy group, more preferably a hydrogen atom or a hydroxyl group.

Examples of the compound (1-1-2) include 3-methoxyphenol, 5-methoxyresorcin, 3-methoxybenzene-1,2-diol, 4-butyl-3-methoxyphenol, 3-methoxy-4-(1-phenylethyl)phenol, and 5-(4-hydroxyphenylethenyl)-1-hydroxy-3-methoxybenzene (trivial name: pinostilbene).

(1-1-3) Resorcin Derivative Represented by the Following Formula (1-1-3)

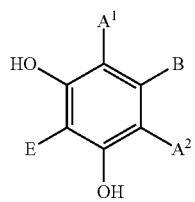

(1-1-3)

wherein $A^1$, $A^2$, B, and E are defined as above.

Examples of the resorcin derivative represented by formula (1-1-3) include the resorcin derivatives represented by the following formula (i) or (ii).

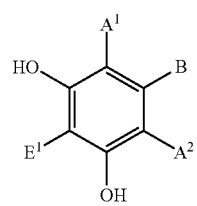

(i)

wherein $A^1$, $A^2$, and B are defined as above; $E^1$ represents a hydroxyl group, a C1 to C6 linear-chain or branched-chain alkyl or alkenyl group, or a C1 to C6 linear-chain or branched-chain alkoxy or alkenyloxy group.

Each of $A^1$ and $A^2$ is preferably a hydrogen atom or a C1 to C12 linear-chain or branched-chain alkyl or alkenyl group, more preferably a hydrogen atom.

B is preferably a hydrogen atom, an optionally substituted C7 to C12 aralkyl or arylalkenyl group, or $-OR^3$ (wherein $R^3$ is a hydrogen atom or a C1 to C4 linear-chain or branched-chain alkyl or alkenyl group).

$E^1$ is preferably a hydroxyl group, a C1 to C4 linear-chain or branched-chain alkyl or alkenyl group, or a C1 to C4 linear-chain or branched-chain alkoxy or alkenyloxy group.

Examples of the resorcin derivative represented by formula (i) include 2-alkylresorcins such as 2-methylresorcin, 2-ethylresorcin, and 2-propylresorcin; pyrogallol; 2-alkoxyresorcins such as 2-methoxyresorcin; gallate esters such as gallic acid, methyl gallate, ethyl gallate, propyl gallate, and butyl gallate; and 5-(phenylethenyl)-2-isopropylresorcin.

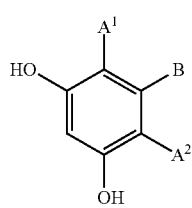

(ii)

wherein $A^1$, $A^2$, and B are defined as above.

The resorcin derivative represented by formula (ii) is more preferably resorcin derivatives represented by formula (ii-1) or (ii-2).

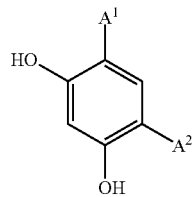

(ii-1)

wherein $A^1$ and $A^2$ are defined as above.

Examples of the resorcin derivative represented by formula (ii-1) include 4-alkylresorcins such as 4-methylresorcin, 4-ethylresorcin, 4-propylresorcin, 4-isopropylresorcin, 4-butylresorcin (trivial name: rucinol), 4-isobutylresorcin, 4-sec-butylresorcin, 4-tert-butylresorcin, 4-pentylresorcin, 4-isopentylresorcin, 4-sec-pentylresorcin, 4-tert-pentylresorcin, 4-neopentylresorcin, 4-hexylresorcin, 4-isohexylresorcin, 4-heptylresorcin, 4-octylresorcin, 4-(2-ethylhexyl)resorcin, 4-nonylresorcin, 4-decylresorcin, 4-undecylresorcin, and 4-dodecylresorcin;

4-alkenylresorcins such as 4-vinylresorcin, 4-allylresorcin, 4-butenylresorcin, 4-hexenylresorcin, and 4-decenylresorcin;

4-aralkylresorcins such as 4-benzylresorcin, 4-(1-phenylethyl)resorcin (trivial name: Symwhite 377), 4-furanylethylresorcin, 4-tetrahydropyranylresorcin, 4-(2-phenylethyl)resorcin, and 4-(3-phenylpropyl)resorcin;

4-hydroxyaralkylresorcins such as 4-(4-hydroxybenzyl)resorcin, 4-(2,4-dihydroxybenzyl)resorcin, 4-(4-hydroxyphenylethyl)resorcin, and 4-(2,4-dihydroxyphenylethyl)resorcin;

4-arylalkenylresorcins such as 4-(1-phenylethenyl)resorcin and 4-(3-phenylpropenyl)resorcin;

4-hydroxyarylalkenylresorcins such as 4-(4-hydroxyphenylethenyl)resorcin and 4-(2,4-dihydroxyphenylethenyl)resorcin;

4-(1-methylnaphthyl)resorcin;

4-alkoxyresorcins such as 4-methoxyresorcin, 4-ethoxyresorcin, 4-isopropoxyresorcin, 4-propoxyresorcin, 4-butoxyresorcin, 4-sec-butoxyresorcin, 4-tert-butoxyresorcin, and 4-pentoxyresorcin;

haloresorcins such as 4-chlororesorcin and 4-bromoresorcin;

4-alkanoylresorcins such as 4-acetylresorcin, 4-propanoylresorcin, 4-butanoylresorcin, 4-pentanoylresorcin, and 4-hexanoylresorcin; and 4-arylalkanoylresorcins such as 4-phenylethanoylresorcin, 4-phenylpropanoylresorcin, 4-phenylbutanoylresorcin, 4-phenylpentanoylresorcin, 4-phenylhexanoylresorcin, 3-(hydroxyphenyl)-1-(2,4-dihydroxyphenyl)propen-1-one (trivial name: isoliquiritigenin).

Among these, from the viewpoint of obtaining more remarkable change of the shape of hair after the treatment using the hair cosmetic composition of the present invention, improving shampooing resistance of shaped hair, obtaining more remarkable change of the shape of hair during semipermanent re-deforming of the shape of hair by heating, and improving shampooing resistance of shaped hair after re-deforming of the shape of hair by means of condensate of component (A) and component (B) formed in the hair, one or more member selected from the group consisting of 4-alkylresorcin, 4-aralkylresorcin and 4-halogenated resorcin is preferable, and one or more member selected from the group consisting of 4-hexylresorcin, Rucinol, Symwhite and 4-chlororesorcin is more preferable.

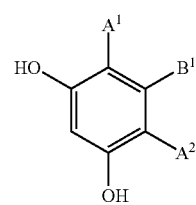

(ii-2)

wherein $A^1$ and $A^2$ are defined as above; $B^1$ represents a C1 to C12 linear-chain or branched-chain alkyl or alkenyl group, an optionally substituted C7 to C12 aralkyl or arylalkenyl group, or $-OR^3$ or $-COOR^3$ (wherein $R^3$ represents a hydrogen atom or a C1 to C6 linear-chain or branched-chain alkyl or alkenyl group).

The resorcin derivative represented by formula (ii-2) is more preferably resorcin derivatives represented by formula (ii-2-a) or (ii-2-b).

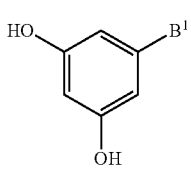

(ii-2-a)

wherein $B^1$ has the same meaning as defined above.

Examples of the resorcin derivative represented by formula (ii-2-a) include 5-alkylresorcins such as 5-methylresorcin, 5-ethylresorcin, 5-propylresorcin, 5-isopropylresorcin, 5-butylresorcin, 5-isobutylresorcin, 5-sec-butylresorcin, 5-tert-butylresorcin, 5-pentylresorcin (trivial name: olivetol), 5-isopentylresorcin, 5-neopentylresorcin, 5-hexylresorcin, 5-isohexylresorcin, 5-heptylresorcin, 5-octylresorcin, 5-(2-ethylhexyl)resorcin, 5-nonylresorcin, 5-decylresorcin, 5-undecylresorcin, and 5-dodecylresorcin;

5-alkenylresorcins such as 5-vinylresorcin, 5-allylresorcin, 5-butenylresorcin, 5-hexenylresorcin, and 5-decenylresorcin;

phloroglucinol;

5-alkoxybenzene-1,3-diols such as 5-ethoxybenzene-1,3-diol, 5-propoxybenzene-1,3-diol, and 5-butoxybenzene-1,3-diol;

3,5-dihydroxybenzoic acid;

3,5-dihydroxybenzoate esters such as methyl 3,5-dihydroxybenzoate, ethyl 3,5-dihydroxybenzoate, propyl 3,5-dihydroxybenzoate, butyl 3,5-dihydroxybenzoate, pentyl 3,5-dihydroxybenzoate, and hexyl 3,5-dihydroxybenzoate;

5-aralkylresorcins such as 5-benzylresorcin, 5-(1-phenylethyl)resorcin, 5-(2-phenylethyl)resorcin, and 5-(phenylpropyl)resorcin;

5-hydroxyaralkylresorcins such as 5-(4-hydroxybenzyl)resorcin, 5-(2,4-dihydroxybenzyl)resorcin, 5-(hydroxyphenylethyl)resorcin (trivial name: dihydroresveratrol), and 5-(2,4-dihydroxyphenylethyl)resorcin;

5-arylalkenylresorcins such as 5-(phenylethenyl)resorcin (trivial name: pinosylvin) and 5-(phenylpropenyl)resorcin; and 5-hydroxyarylalkenylresorcins such as 5-(4-hydroxyphenylethenyl)resorcin (trivial name: resveratrol), 5-(4-methoxyphenylethenyl)resorcin (trivial name: 4-methoxyresveratrol), 5-(2,4-dihydroxyphenylethenyl)resorcin (trivial name: oxyresveratrol), 5-(2-methoxy-4-hydroxyphenylethenyl)resorcin (trivial name: gnetucleistol D), 5-(3,4-dimethoxyphenylethenyl)resorcin (trivial name: gnetucleistol E), 5-(3-hydroxy-4-methoxyphenylethenyl)resorcin (trivial name: rhapontigenin), 5-(4-hydroxy-3-methoxyphenylethenyl)resorcin (trivial name: isorhapontigenin), and 5-(dihydroxyphenylethenyl)resorcin (trivial name: piceatannol).

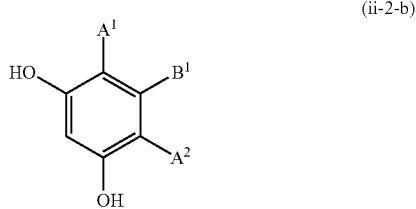

(ii-2-b)

wherein $A^1$, $A^2$, and $B^1$ are defined as above.

Each of $A^1$ and $A^2$ is preferably a hydrogen atom, a C1 to C4 linear-chain or branched-chain alkyl or alkenyl group, or a C1 to C4 alkoxy or alkenyloxy group.

Examples of the resorcin derivative represented by formula (ii-2-b) include 2-alkylbenzene-1,3,5-triols such as 2-methylbenzene-1,3,5-triol, 2-ethylbenzene-1,3,5-triol, 2-propylbenzene-1,3,5-triol, 2-butylbenzene-1,3,5-triol, 2-hexylbenzene-1,3,5-triol, 2-octylbenzene-1,3,5-triol, and 2-dodecylbenzene-1,3,5-triol;

2-aralkyl-1,3,5-triols such as 2-benzylbenzene-1,3,5-triol, 2-(phenylethyl)benzene-1,3,5-triol, and 2-(phenylpropyl)benzene-1,3,5-triol;

2,4,6-trihydroxyphenylaralkylketone such as 2-acetylbenzene-1,3,5-triol, 2-propanoylbenzene-1,3,5-triol, 2-butanoylbenzene-1,3,5-triol, 2-phenylethanoylbenzene-1,3,5-triol, 2-hydroxyphenyl-1-(benzene-2,4,6-triol)ethan-1-one, 3-hydroxyphenyl-1-(benzene-2,4,6-triol)propan-1-one (trivial name: phloretin), 4-hydroxyphenyl-1-(benzene-2,4,6-triol)butan-1-one, 2-benzoylbenzene-1,3,5-triol, 2-(hydroxybenzoyl)benzene-1,3,5-triol, 2-(3,5-dihydroxybenzoyl)benzene-1,3,5-triol, and 2-(2,4-dihydroxybenzoyl)benzene-1,3,5-triol; and 3,5-dihydroxybenzoate esters such as 3,5-dihydroxy-2-methylbenzoic acid, methyl 3,5-dihydroxy-2-methylbenzoate, 3,5-dihydroxy-2-ethylbenzoic acid, methyl 3,5-dihydroxy-2-ethylbenzoate, 3,5-dihydroxy-2-propylbenzoic acid, methyl 3,5-dihydroxy-2-propylbenzoate, 3,5-dihydroxy-2-butylbenzoic acid, and methyl 3,5-dihydroxy-2-butylbenzoate.

Examples of the benzophenone derivative represented by formula (1-2) include 4-benzoylresorcin (trivial name: Benzophenone-1), 4-(hydroxybenzoyl)resorcin, 4-(dihydroxybenzoyl)resorcin, 4-(2,4-dihydroxybenzoyl)resorcin (trivial name: Benzophenone-2), 4-(methylbenzoyl)resorcin, 4-(ethylbenzoyl)resorcin, 4-(dimethylbenzoyl)resorcin, 4-(diethylbenzoyl)resorcin, 4-naphthoylresorcin, 2-hydroxy-4-methoxybenzophenone (trivial name: Benzophenone-3), 2,2'-dihydroxy-4,4'-dimethoxybenzophenone (trivial name: Benzophenone-6), 2,2'-dihydroxy-4-methoxybenzophenone (trivial name: Benzophenone-8), 2-hydroxy-4-methoxy-4'-methylbenzophenone (trivial name: Benzophenone-10), and 2-hydroxy-4-octyloxybenzophenone (trivial name: Benzophenone-12).

Among the naphthol derivatives represented by formula (1-3-a) or (1-3-b), preferred are those represented by formula (1-3-a) or (1-3-b) in which $R^1$ is a hydrogen atom or a C1 to C4 alkyl or alkenyl group, with a hydrogen atom being more preferred.

Also, in the above naphthol derivatives, each of $A^1$ and $A^2$ is preferably a hydrogen atom, a hydroxyl group, a C1 to C4 linear-chain or branched-chain alkyl group, or a C1 to C4 alkoxy group, more preferably a hydrogen atom or a hydroxyl group.

Also, in the above naphthol derivatives, D is preferably a hydrogen atom, a hydroxyl group, a C1 to C4 linear-chain or branched-chain alkyl group, or a C1 to C4 alkoxy group.

Also, in the above naphthol derivatives, E is preferably a hydrogen atom, a hydroxyl group, a C1 to C4 alkyl group, or a C1 to C4 alkoxy group.

Examples of the above compounds include 1-naphthol, 2-naphthol, 3-methylnaphthalen-1-ol, naphthalene-1,4-diol, naphthalene-1,5-diol, and naphthalene-1,8-diol.

Among the compounds represented by formula (1), preferred are m-dimethoxybenzene derivatives represented by formula (1-1-1), resorcin derivatives represented by formula (1-1-3), benzophenone derivatives represented by formula (1-2), and naphthol derivative represented by formula (1-3-a) or (1-3-b). More preferred compounds are 2-methylresorcin, 4-chlororesorcin, 4-alkylresorcin, 4-aralkylresorcin, 4-acylated resorcin, 5-alkylresorcin, 5-aralkylresorcin, 5-hydroxyarylalkenylresorcin, a 2,4,6-trihydroxyphenylaralkylketone, gallic acid, and a gallate ester. Still more preferred compounds are 4-butylresorcin (trivial name: rucinol), 4-hexylresorcin, 4-(1-phenylethyl)resorcin (trivial name: Symwhite 377), 4-furanylethylresorcin, 4-tetrahydropyranylresorcin, 5-(hydroxyphenylethenyl)resorcin (trivial name: resveratrol), 3-hydroxyphenyl-1-(benzene-2,4,6-triol)propan-1-one (trivial name: phloretin), 4-(2,4-dihydroxybenzoyl)resorcin (trivial name: Benzophenone-2), 5-(hydroxyphenylethenyl)-1,3-dimethoxybenzene (trivial name: pterostilbene), and 1-naphthol. Yet more preferred compounds are 2-methylresorcin, 4-chlororesorcin, 1-naphthol, 4-n-butylresorcin, 4-(1-phenylethyl)resorcin, 5-(hydroxyphenylethenyl)resorcin, 3-hydroxyphenyl-1-(benzene-2,4,6-triol)propan-1-one, and 4-(2,4-dihydroxybenzoyl) resorcin.

In addition, among the compound represented by general formula (1), obtaining more remarkable change of the shape of hair after the treatment using the hair cosmetic composition of the present invention, as well as improving restoration of damaged hair damaged by chemical treatment, by means of condensate of component (A) and component (B) formed in the hair, one or more member selected from the group consisting of m-dimethoxybenzene derivatives represented by general formula (1-1-1), resorcin derivatives represented by general formula (1-1-3), benzophenone derivatives represented by general formula (1-2), and naphthol derivatives represented by general formula (1-3-a) or (1-3-b) is preferable.

Furthermore, one or more member selected from the group consisting of 2-alkylresorcin, 4-alkylresorcin, 4-aralkyl resorcin, 4-halogenated resorcin, 5-hydroxyarylalkenylresorcin, 2,4,6-trihydroxyphenylaralkylketone, benzophenone derivative, naphthol, 4-acylated resorcin, 5-alkylresorcin, 5-aralkylresorcin, gallic acid and gallic acid ester is preferable.

Furthermore, one or more member selected from the group consisting of 2-methylresorcin, 4-butylresorcin (trivial name: Rucinol), 4-hexylresorcin, 4-(1-phenylethyl)resorcin (trivial name: Symwhite377), 4-chlororesorcin, 5-(hydroxyphenylethenyl)resorcin (trivial name: resveratrol), 5-(hydroxyphenylethenyl)-1,3-dimethoxybenzene (trivial name: Pterostilbene), 3-hydroxyphenyl-1-(benzene-2,4,6-triol)propane-1-on (trivial name: Phloretin), 4-(2,4-dihydroxybenzoyl)resorcin (trivial name: Benzophenone-2) and 1-naphthol is preferable.

The compound represented by formula (1) preferably has a molecular weight of 120 or higher, and from the viewpoint of permeability to hair, 1,000 or lower, more preferably 500 or lower, still more preferably 300 or lower.

Component (B3) is a compound represented by the following formula (2).

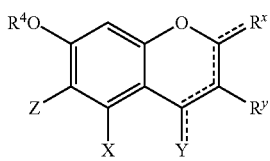

(2)

wherein, $R^4$ represents a hydrogen atom or a methyl group;

X represents a hydrogen atom, a hydroxyl group, or a methoxy group;

Y represents a hydrogen atom, an oxygen atom, a hydroxyl group, or a methoxy group;

Z represents a hydrogen atom or a C1 to C5 linear-chain or branched-chain alkyl or alkenyl group;

$R^x$ represents a hydrogen atom, an oxygen atom, a hydroxyl group, a methoxy group, or an aromatic hydrocarbon group which may be substituted with 1 to 3 hydroxyl groups or methoxy groups and which optionally forms a condensed ring with 1,3-dioxolane;

$R^y$ represents a hydrogen atom, a hydroxyl group, a methoxy group, an aromatic hydrocarbon group which may be substituted with 1 to 3 hydroxyl groups or methoxy groups, to thereby form a condensed ring with 1,3-dioxolane, or an arylcarbonyloxy or aralkylcarbonyloxy group which may be substituted with 1 to 3 hydroxyl groups or methoxy groups;

a dotted line portion may be a double bond;

each of the combinations of the dotted line and the solid line being adjacent to $R^x$ or Y denotes a double bond in the case where $R^x$ or Y is an oxygen atom, and denotes a single bond in the other cases; and Z represents a C1 to C5 linear-chain or branched-chain alkyl or alkenyl group, only when $R^x$ or $R^y$ is an o,p-dihydroxyaromatic hydrocarbon group, and represents a hydrogen atom in the other cases.

Examples of the C1 to C5 linear-chain or branched-chain alkyl or alkenyl group of Z include methyl, ethyl, n-propyl, isopropyl, n-butyl, isobutyl, sec-butyl, tert-butyl, n-pentyl, isopentyl, sec-pentyl, tert-pentyl, neopentyl, 1-methylpentyl, vinyl, allyl, and butenyl.

Examples of the aromatic hydrocarbon group of $R^x$ or $R^y$ include phenyl and naphthyl. Examples of the aromatic hydrocarbon group which forms a condensed ring with 1,3-dioxolane include 1,3-benzodioxol-5-yl group.

Examples of the arylcarbonyloxy group of $R^y$ include a benzoyloxy group, and examples of the aralkylcarbonyloxy group of $R^y$ include a benzylcarbonyloxy group, a phenylethylcarbonyloxy group, a phenylpropylcarbonyloxy group, and a phenylbutylcarbonyloxy group.

Specific examples of the compound represented by formula (2) include compounds represented by the following formulas (2-1) to (2-5).

(2-1) Flavanols Represented by the Following Formula (2-1)

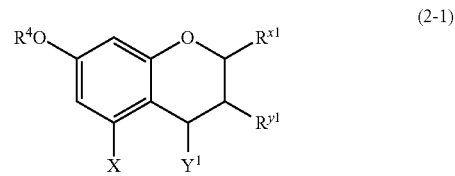

(2-1)

wherein $R^4$ and X are defined as above;

$Y^1$ represents a hydrogen atom, a hydroxyl group, or a methoxy group;

$R^{x1}$ represents an aromatic hydrocarbon group which may be substituted with 1 to 3 hydroxyl groups or methoxy groups and which optionally forms a condensed ring with 1,3-dioxolane; and $R^{y1}$ represents a hydrogen atom, a hydroxyl group, a methoxy group, an aromatic hydrocarbon group which may be substituted with 1 to 3 hydroxyl groups or methoxy groups and which optionally forms a condensed ring with 1,3-dioxolane, or an arylcarbonyloxy or aralkylcarbonyloxy group which may be substituted with 1 to 3 hydroxyl groups or methoxy groups.

(2-2) Flavanones or Flavanonol Represented by the Following Formula (2-2)

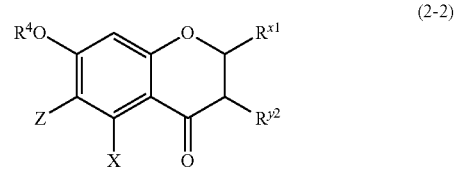

(2-2)

wherein $R^4$, X, Z, and $R^{x1}$ are defined as above, and $R^{y2}$ represents a hydrogen atom, a hydroxyl group, or a methoxy group; and Z represents a C1 to C5 linear-chain or branched-chain alkyl or alkenyl group, only when $R^{x1}$ is an o,p-dihydroxyaromatic hydrocarbon group, and represents a hydrogen atom in the other cases.

(2-3) Flavanones or Flavanonol Represented by the Following Formula (2-3)

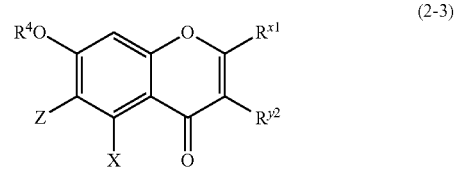

(2-3)

wherein $R^4$, X, Z, $R^{x1}$, and $R^{y2}$ are defined as above. Z is a C1 to C5 linear-chain or branched-chain alkyl or alkenyl group, only when $R^{x1}$ is an o,p-dihydroxyaromatic hydrocarbon group. In the other cases, Z is a hydrogen atom.

(2-4) Isoflavons and Isoflavans Represented by the Following Formula (2-4)

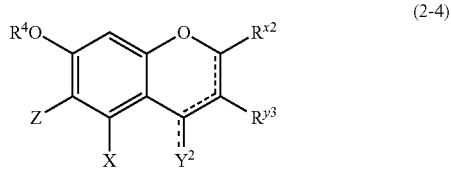

wherein
$R^4$, X, Z, and the dotted line are defined as above;
$Y^2$ represents a hydrogen atom or an oxygen atom;
$R^{x2}$ represents a hydrogen atom, a hydroxyl group, or a methoxy group;
$R^{y3}$ represents an aromatic hydrocarbon group which may be substituted with 1 to 3 hydroxyl groups or methoxy groups and which optionally forms a condensed ring with 1,3-dioxolane; the combination of the dotted line and the solid line being adjacent to $Y^2$ denotes a double bond in the case where $Y^2$ is an oxygen atom, and denotes a single bond in the other cases; and
Z represents a C1 to C5 linear-chain or branched-chain alkyl or alkenyl group, only when $R^{y3}$ is an o,p-dihydroxyaromatic hydrocarbon group, and represents a hydrogen atom in the other cases.

(2-5) Coumarins Represented by Formula (2-5)

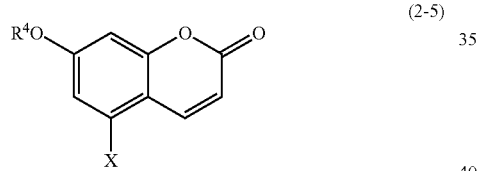

wherein $R^4$ and X are defined as above.

The compound (2-1) is preferably compound represented by the following formula (2-1-A) to (2-1-C).

(2-1-A) Flavan-3-ols Represented by the Following Formula (2-1-A)

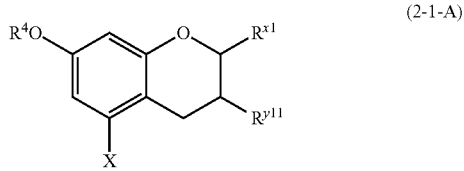

wherein $R^4$, X, and $R^{x1}$ are defined as above; $R^{y11}$ represents a hydroxyl group, a methoxy group, an aromatic hydrocarbon group which may be substituted with 1 to 3 hydroxyl groups or methoxy groups and which optionally forms a condensed ring with 1,3-dioxolane, or an arylcarbonyloxy or aralkylcarbonyloxy group which may be substituted with 1 to 3 hydroxyl groups or methoxy groups.

The flavan-3-ols represented by formula (2-1-A) are preferably those in which $R^4$ and X are the same as defined above; $R^{x1}$ is an aromatic hydrocarbon group which may be substituted with 1 to 3 hydroxyl groups or methoxy groups; $R^{y1}$ is a hydrogen atom, a hydroxyl group, a methoxy group, or an arylcarbonyloxy or aralkylcarbonyloxy group which may be substituted with 1 to 3 hydroxyl groups or methoxy groups.

Examples of the compound of (2-1-A) include catechin, epicatechin, epigallocatechin, meciadanol, afzelechin, epiafzelechin, catechin gallate, epicatechin gallate, epigallocatechin gallate, phylloflavan, fisetinidol, guibourtinidol, and robinetinidol.

(2-1-B) Flavan-4-ols Represented by the Following Formula (2-1-B)

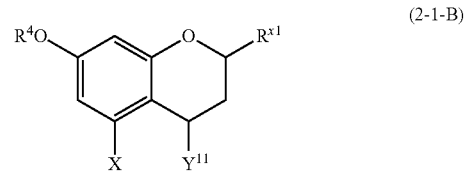

wherein $R^4$, X, and $R^{x1}$ are defined as above, and $Y^{11}$ represents a hydroxyl group or a methoxy group The flavan-4-ol represented by formula (2-1-B) is preferably a compound wherein $R^4$ and X are defined as above, $Y^{11}$ is a hydroxyl group, and $R^{x1}$ is an aromatic hydrocarbon group which may be substituted with 1 to 3 hydroxyl groups or methoxy groups.

Examples of the compound of (2-1-B) include apiforol and luteoforol.

(2-1-C) Flavan-3,4-diols Represented by the Following Formula (2-1-C)

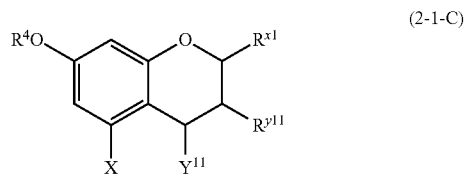

wherein $R^4$, X, $Y^{11}$, $R^{x1}$, and $R^{y11}$ are defined as above.

The flavane-3,4-diol represented by formula (2-1-C) is preferably a compound wherein $R^4$ and X are defined as above; $Y^{11}$ is a hydroxyl group or a methoxy group; $R^{x1}$ is an aromatic hydrocarbon group which may be substituted with 1 to 3 hydroxyl groups or methoxy groups; and $R^{y1}$ is a hydroxyl group or a methoxy group.

Examples of the compound of (2-1-C) include leucocyanidin, leucodelphinidin, leucopelargonidin, leucopeonidin, and leucofisetinidin.

The compound of (2-2) is preferably any of the compounds represented by the following formula (2-2-A) or (2-2-B).

(2-2-A) Flavanones Represented by the Following Formula (2-2-A)

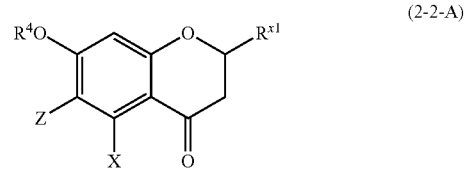

wherein $R^4$, X, Z, and $R^{x1}$ are defined as above, and

Z represents a C1 to C5 linear-chain or branched-chain alkyl or alkenyl group, only when $R^{x1}$ is an o,p-dihydroxyaromatic hydrocarbon group, and represents a hydrogen atom in the other cases.

The flavanone represented by formula (2-2-A) is preferably a compound wherein $R^4$ and X are defined as above; Z is a hydrogen atom; and $R^{x1}$ is an aromatic hydrocarbon group which may be substituted with 1 to 3 hydroxyl groups or methoxy groups; and $R^{y1}$ is a hydroxyl group or a methoxy group.

Examples of the compound of (2-2-A) include eriodictyol, naringenin, pinocembrin, hesperetin, homoeriodictyol, isosakuranetin, sterubin, sakuranetin, alpinetin, and butin.

(2-2-B) Flavanonols Represented by the Following Formula (2-2-B)

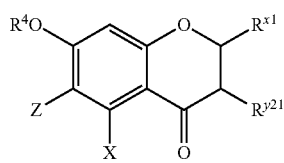

(2-2-B)

wherein $R^4$, X, Z, and $R^{x1}$ are defined as above; $R^{y21}$ represents a hydroxyl group or a methoxy group;

Z represents a C1 to C5 linear-chain or branched-chain alkyl or alkenyl group, only when $R^{x1}$ is an o,p-dihydroxyaromatic hydrocarbon group, and represents a hydrogen atom in the other cases.

The flavanonol represented by formula (2-2-B) is preferably a compound wherein $R^4$ and X are defined as above; Z is a hydrogen atom; $R^{x1}$ is an aromatic hydrocarbon group which may be substituted with 1 to 3 hydroxyl groups or methoxy groups; and $R^{y1}$ is a hydroxyl group or a methoxy group.

Examples of the compound of (2-2-B) include aromadendrin, taxifolin, and dihydrokaempferide.

The compound of (2-3) is preferably any of the compounds represented by the following formula (2-3-A) or (2-3-B).

(2-3-A) Flavones Represented by the Following Formula (2-3-A)

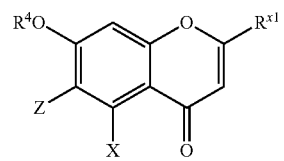

(2-3-A)

wherein $R^4$, X, Z, and $R^{x1}$ are defined as above; and

Z represents a C1 to C5 linear-chain or branched-chain alkyl or alkenyl group, only when $R^{x1}$ is an o,p-dihydroxyaromatic hydrocarbon group, and represents a hydrogen atom in the other cases.

The flavone represented by formula (2-3-A) is preferably a compound wherein $R^4$ and X are defined as above; Z is a hydrogen atom; and $R^{x1}$ is an aromatic hydrocarbon group which may be substituted with 1 to 3 hydroxyl groups or methoxy groups.

Examples of the compound of (2-3-A) include luteolin, apigenin, chrysin, norartocarpetin, tricetin, diosmetin, acacetin, chrysoeriol, genkwanin, techtochrysin, tricin, 4',7-dihydroxyflavone, and pratol.

(2-3-B) Flavonols Represented by Following Formula (2-3-B)

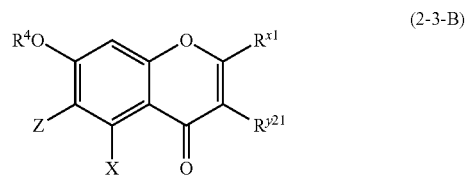

(2-3-B)

wherein $R^4$, X, Z, $R^{x1}$, and $R^{y21}$ are defined as above; and

Z represents a C1 to C5 linear-chain or branched-chain alkyl or alkenyl group, only when $R^{x1}$ is an o,p-dihydroxyaromatic hydrocarbon group, and represents a hydrogen atom in the other cases.

The flavonol represented by formula (2-3-B) is preferably a compound wherein $R^4$ and X are defined as above; Z is a hydrogen atom; $R^{x1}$ is an aromatic hydrocarbon group which may be substituted with 1 to 3 hydroxyl groups or methoxy groups; and $R^{y1}$ is a hydroxyl group or a methoxy group.

Examples of the compound of (2-3-B) include quercetin, myricetin, morin, kaempferol, galangin, kaempferide, tamarixetin, laricitrin, annulatin, isorhamnetin, syringetin, rhamnetin, europetin, azaleatin, 5-O-methylmyricetin, retusin, pachypodol, rhamnazin, ayanin, ombuin, and fisetin.

The compound of (2-4) is preferably any of the compounds represented by the following formula (2-4-A) to (2-4-C).

(2-4-A) Isoflavones Represented by the Following Formula (2-4-A)

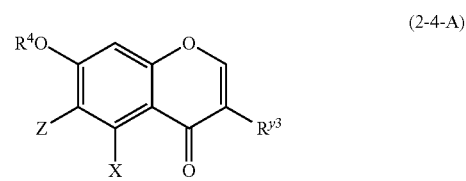

(2-4-A)

wherein $R^4$, X, Z, and $R^{y3}$ are defined as above; and

Z represents a C1 to C5 linear-chain or branched-chain alkyl or alkenyl group, only when $R^{y3}$ is an o,p-dihydroxyaromatic hydrocarbon group, and represents a hydrogen atom in the other cases.

The isoflavone represented by formula (2-4-A) is preferably a compound wherein $R^4$ and X are defined as above; Z is a hydrogen atom or a C1 to C5 linear-chain or branched-chain alkyl or alkenyl group; and $R^{y3}$ is an aromatic hydrocarbon group which may be substituted with 1 to 3 hydroxyl groups or methoxy groups and optionally forms a condensed ring with 1,3-dioxolane.

Examples of the compound of (2-4-A) include genistein, daidzein, orobol, biochanin A, pratensein, 5-O-methylgenistein, prunetin, calycosin, formononetin, 7-O-methylluteone, luteone, and pseudobaptigenin.

(2-4-B) Isoflavans Represented by the Following Formula (2-4-B)

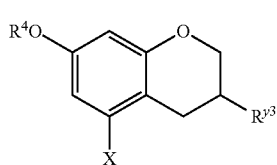

wherein $R^4$, X, and $R^{y3}$ are defined as above.

The isoflavan represented by formula (2-4-B) is preferably a compound wherein $R^4$ and X are defined as above; and $R^{y3}$ is an aromatic hydrocarbon group which may be substituted with 1 to 3 hydroxyl groups or methoxy groups and optionally forms a condensed ring with 1,3-dioxolane.

Examples of the compound of (2-4-B) include equol.

(2-4-C) Isoflavenes Represented by the Following Formula (2-4-C)

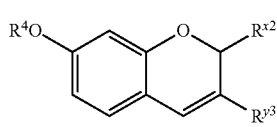

wherein $R^4$, $R^{x2}$, and $R^{y3}$ are defined as above.

The isoflavene represented by formula (2-4-C) is preferably a compound wherein $R^4$ and $R^{x2}$ are defined as above; and $R^{y3}$ is an aromatic hydrocarbon group which may be substituted with 1 to 3 hydroxyl groups or methoxy groups and optionally forms a condensed ring with 1,3-dioxolane.

Examples of the compound of (2-4-C) include haginin D, haginin E, and 2-methoxyjudaicin.

Examples of the compound (2-5) include umbelliferone.

Among the aforementioned compounds represented by formula (2), preferred compounds are flavan-3-ols represented by formula (2-1-A), flavonols represented by formula (2-3-B), flavanones represented by formula (2-2-A), flavones represented by formula (2-3-A), isoflavones represented by formula (2-4-A), isoflavans represented by formula (2-4-B), and coumarins represented by formula (2-5). Specific examples of more preferred compounds include catechin, epicatechin, epigallocatechin, catechin gallate, epicatechin gallate, epigallocatechin gallate, quercetin, morin, hesperetin, naringenin, chrysin, daidzein, equol, and umbelliferone. Of these, catechin, epigallocatechin, epigallocatechin gallate, naringenin, and equol are yet more preferred. Mixtures such as a green tea, containing the aforementioned compounds, may also be used.

Each of the compounds represented by formula (2) preferably has a molecular weight of 150 or higher. From the viewpoint of permeability to hair, the molecular weight is preferably 1,000 or lower, more preferably 700 or lower, still more preferably 500 or lower.

Among the component (B), from the viewpoint of obtaining more remarkable change of the shape of hair after the treatment using the hair cosmetic composition of the present invention, improving shampooing resistance of shaped hair, obtaining more remarkable change of the shape of hair during semipermanent re-deforming of the shape of hair by heating, and improving shampooing resistance of shaped hair after re-deforming of the shape of hair by means of condensate of component (A) and component (B) formed in the hair, one or more member selected from the group consisting of resorcin derivatives represented by general formula (ii-1), m-dimethoxybenzene derivatives represented by general formula (1-1-1), resorcin derivatives represented by general formula (1-1-3), benzophenone derivatives represented by general formula (1-2), naphthol derivatives represented by general formula (1-3-a) or (1-3-b), flavan-3-ols represented by general formula (2-1-A), flavonols represented by general formula (2-3-B), flavanones represented by general formula (2-2-A), flavones represented by general formula (2-3-A), isoflavones represented by general formula (2-4-A), isoflavans represented by general formula (2-4-B) and coumarins represented by general formula (2-5) is preferable, and favorable compounds classified in each component is as described above.

Subcomponents of component (B) may be used singly or in combination of two or more species. Two or more of (B1) to (B3) may be used in combination. In the present invention, (B2) or (B3) is preferred, from the viewpoint of more consistently deforming hair.

In order to attain a remarkable change in hair shape after treatment with the hair cosmetic composition of the present invention, to further enhance the resistance of the hair shape to shampooing, to attain a more remarkable change in hair shape upon semi-permanently re-deforming of hair through heating, and to further enhance the resistance of the re-deformed hair to shampooing, the hair cosmetic composition of the present invention preferably has a total component (B) content, relative to the total hair cosmetic composition, of 0.2 mass % or higher, more preferably 0.5 mass % or higher, still more preferably 1.0 mass % or higher, yet more preferably 1.5 mass % or higher. In addition to the aforementioned viewpoints, in order to suitably mix components, the total component (B) content is preferably 40 mass % or lower, more preferably 30 mass % or lower, still more preferably 25 mass % or lower, yet more preferably 23 mass % or lower, further more preferably 20 mass % or lower.

In the case where component (B1) is used as component (B), the component (B1) content (i.e., the preferred component (B) content) of the hair cosmetic composition of the present invention, relative to the total hair cosmetic composition, is more preferably 2 mass % or higher, still more preferably 3 mass % or higher, yet more preferably 4 mass % or higher, further more preferably 5 mass % or higher, and in order to suitably mix components, more preferably 17 mass % or lower.

In the case where component (B2) is used as component (B), the component (B2) content (i.e., the preferred component (B) content) is more preferably 2 mass % or higher, and in order to suitably mix components, more preferably 17 mass % or lower, still more preferably 15 mass % or lower, yet more preferably 12 mass % or lower.

In the case where component (B3) is used as component (B), the component (B3) content (i.e., the preferred component (B) content) of the hair cosmetic composition of the present invention is more preferably 17 mass % or lower, still more preferably 15 mass % or lower, yet more preferably 12 mass % or lower, in order to suitably mix components.

In order to attain a remarkable change in hair shape after treatment with the hair cosmetic composition of the present invention by a condensation product between component (A) and component (B) formed in hair shafts, to further enhance the resistance of the hair shape to shampooing, to attain a more remarkable change in hair shape upon semi-permanently re-deforming of hair through heating, and to further enhance the resistance of the re-deformed hair to shampooing, the molar ratio of component (B) to component (A), (B)/(A), of the hair cosmetic composition of the present invention applied to hair is preferably 0.001 or higher, more preferably 0.1 or higher, still more preferably 0.2 or higher, yet more preferably 0.25 or higher, and preferably lower than 2.5, more preferably 2.3 or lower, still more preferably 2.1 or lower, yet more preferably 1.9 or lower, further more preferably 1.7 or lower, further more preferably 1.6 or lower.

In the case where component (B1) is used as component (B), the molar ratio of component (B1) to component (A), (B1)/(A), of the hair cosmetic composition of the present invention applied to hair is preferably 0.2 or higher, more preferably 0.3 or higher, still more preferably 0.4 or higher, yet more preferably 0.5 or higher, further more preferably 0.7 or higher, and preferably lower than 2.5, more preferably 2.3 or lower, still more preferably 2.0 or lower, yet more preferably 1.5 or lower, further more preferably 1.2 or lower.

In the case where component (B2) is used as component (B), the molar ratio of component (B2) to component (A), (B2)/(A), of the hair cosmetic composition of the present invention applied to hair is preferably 0.001 or higher, more preferably 0.1 or higher, still more preferably 0.2 or higher, yet more preferably 0.25 or higher, and preferably lower than 2.5, more preferably 2.3 or lower, still more preferably 2.0 or lower, yet more preferably 1.5 or lower, further more preferably 1.2 or lower.

In the case where component (B3) is used as component (B), the molar ratio of component (B3) to component (A), (B3)/(A), of the hair cosmetic composition of the present invention applied to hair is preferably 0.001 or higher, more preferably 0.1 or higher, still more preferably 0.2 or higher, yet more preferably 0.25 or higher, and preferably lower than 2.5, more preferably 2.3 or lower, still more preferably 2.0 or lower, yet more preferably 1.5 or lower.

[Component (C): Organic Solvent Having a Boiling Point of 100° C. or Higher at 1,013.25 hPa]

Component (C) is an organic solvent having a boiling point of 100° C. or higher at 1,013.25 hPa. Examples of component (C) include the compounds selected from the following (c1) to (c5).

(c1) Compounds represented by formula (3)

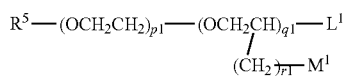

(wherein $R^5$ represents a group $R^6$-Ph-$R^7$— (wherein $R^6$ represents a hydrogen atom, a methyl group, or a methoxy group; $R^7$ represents a chemical bond or a C1 to C3 saturated or unsaturated divalent hydrocarbon group; and Ph represents a p-phenylene group); $L^1$ and $M^1$ each represent a hydrogen atom or a hydroxyl group; and each of $p^1$, $q^1$, and $r^1$ is an integer of 0 to 5, wherein, in the case of $p^1=q^1=0$, $L^1$ is a hydroxyl group, and $R^5$ is not a group $R^6$-Ph-)

(c2) Compounds represented by formula (4)

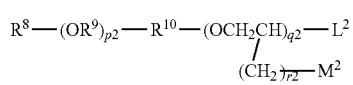

(wherein $R^8$ represents a hydrogen atom or a C1 to C12 linear-chain or branched-chain alkyl group; $R^9$ represents a C1 to C10 linear-chain or branched-chain saturated divalent hydrocarbon group optionally substituted with one hydroxyl group; $R^{10}$ represents a chemical bond or a C1 to C5 linear-chain or branched-chain divalent saturated hydrocarbon group optionally substituted with one [CH$_2$CH(Q)O]$_s$ (wherein Q represents a hydrogen atom or a methyl group, and s is an integer of 1 to 20); $L^2$ represents a hydrogen atom, a hydroxyl group, a C1 to C10 linear-chain or branched-chain alkoxy group or a phenoxy group; $M^2$ represents a hydrogen atom or a hydroxyl group; each of $p^2$ and $q^2$ is an integer of 0 to 20; and $r^2$ is an integer of 0 to 10)

(c3) N-alkyl- or N-alkenylpyrrolidones in which a C1 to C18 alkyl or alkenyl group is bonded to the nitrogen atom (c4) C3 or C4 alkylene carbonates optionally substituted with a hydroxyl group (c5) Lactones or cyclic ketones represented by formula (5), (6), or (7)

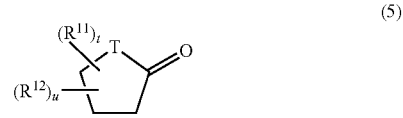

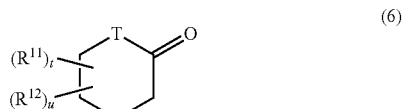

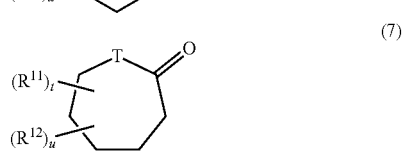

(wherein T represents a methylene group or an oxygen atom; $R^{11}$ and $R^{12}$ are substituents which are different from each other; and each of t and u is 0 or 1)

Examples of organic solvents of component (C) are as follows.

Examples of (c1) include benzyl alcohol, benzyl glycol, PEG-2 benzyl ether, PEG-2 phenyl ether, phenethyl alcohol, phenoxyisopropanol, phenoxypropanediol, phenylpropanol, PPG-2 phenyl ether, cinnamyl alcohol, p-anisyl alcohol, p-methylbenzyl alcohol, and phenoxyethanol.

Examples of (c2) include 1,10-decanediol, 1,2,6-hexanetriol, 1,2-butanediol, 1,2-hexanediol, 1,4-butanediol, 1,5-pentanediol, 2,3-butanediol, 3-methoxybutanol, buteth-3, butoxy diglycol, butoxyethanol, butylene glycol, butyloctanol, dibutoxymethane, diethoxy diglycol, diethylene glycol, diglycerin, dimethoxy diglycol, dipropylene glycol, dipropylene glycol dimethyl ether, ethoxy diglycol, ethoxyethanol, ethylhexanediol, glycerin, glycol, hexanediol, hexyl alcohol, hexylene glycol, hexyloxyethanol, isobutoxypropanol, isopentyldiol, methoxy PEG-10, methoxy PEG-16, methoxy PEG-7, methoxy diglycol, methoxyethanol, methoxyisopropanol, methoxymethylbutanol, methyl hexyl ether, methylpropanediol, n-butyl alcohol, neopentyl glycol, PEG/PPG-1/2 copolymer, PEG-10 propylene glycol, PEG-15 butanediol, PEG-3 methyl ether, PEG-4, PEG-4 methyl ether, PEG-6, PEG-6 methyl ether, PEG-7, PEG-7 methyl ether, PEG-8, PEG-10, PEG-12, pentylene glycol, isopentylene glycol, isoprene glycol (isopentyl diol), poly(1,2-butanediol)-6 propylene glycol, polypropanediol, PPG-10 butanediol, PPG-2 butyl ether, PPG-2 methyl ether, PPG-2 propyl ether, PPG-2-buteth-3, PPG-3, PPG-3 butyl ether, PPG-3 methyl ether, PPG-3-buteth-5, PPG-4 methyl ether, PPG-5-buteth-7, PPG-6, PPG-7, PPG-7-buteth-4, PPG-9, PPG-16, PPG-20, PPG-34, propanediol, propylene glycol, propylene glycol butyl ether, propylene glycol propyl ether, propylene glycol t-butyl ether, sec-butyl alcohol, t-butyl alcohol, t-butylmethyl ether, trimethylpentanol hydroxyethyl ether, trimethyl-1,3-pentanediol, trimethylhexanol, trimethylolpropane, ethylhexyl glycerin, PPG-10 glyceryl ether, and propylal (dipropoxymethane).

Examples of (c3) include N-methylpyrrolidone, N-ethylpyrrolidone, N-octylpyrrolidone, and N-laurylpyrrolidone.

Examples of (c4) include ethylene carbonate, propylene carbonate, and hydroxypropylene carbonate.

In (c5), each of $R^{11}$ and $R^{12}$ in formulas (5) to (7) is preferably a linear-chain, branched-chain, or cyclic alkyl group, a hydroxyl group, a sulfonate group, a phosphate group, a carboxyl group, a phenyl group, a sulfoalkyl group, a phosphoalkyl group, a carboxyalkyl group, or the like. In the case of γ-lactone, the substitution position is preferably the γ position, whereas in case of δ-lactone, the substitution position is preferably the δ position (i.e., the methylene adjacent to the hetero oxygen atom). The substituent is preferably a C1 to C6 linear-chain or branched-chain alkyl group (e.g., methyl, ethyl, propyl, isopropyl, or butyl). For elevating the water-solubility of the lactone or cyclic ketone, $R^{11}$ or $R^{12}$ is preferably an acidic group such as a sulfonate group, a phosphate group, or a carboxyl group, or an alkyl group having such an acidic group as a substituent. Among lactones of (c5), examples of preferred lactones include γ-butyrolactone, γ-caprolactone, γ-valerolactone, δ-valerolactone, δ-caprolactone, and δ-heptanolactone. From the viewpoint of stability of lactone, γ-lactone is more preferred, with γ-butyrolactone and γ-caprolactone being still more preferred. Examples of the cyclic ketone include cyclopentanone, cyclohexanone, cycloheptanone, and 4-methylcycloheptanone. Of these, preferred species of component (C) include benzyl alcohol, phenoxyethanol, 1,2-butanediol, dipropylene glycol, glycerin, PEG-8, PPG-9, propylene glycol, and ethylhexyl glycerin.

From the viewpoint of imparting soft touch feeling to the treated hair, the boiling point of the organic solvent of component (C), as measured at 1,013.25 hPa, is 100° C. or higher, preferably 120° C. or higher, more preferably 150° C. or higher, still more preferably 180° C. or higher. No particular limitation is imposed on the upper limit of the boiling point, so long as the solvent is an organic compound which is liquid at room temperature.

From the viewpoint of promoting permeation of Components (A) and (B), the octanol-water partition coefficient (log P) of component (C) at 25° C. is preferably lower than 10, more preferably 5 or lower, still more preferably 4 or lower, yet more preferably 3 or lower, further more preferably 2 or lower, and preferably −2 or higher, more preferably −1 or higher. The parameter "log P" is an index for the distribution of a substance between an octanol phase and an aqueous phase and is defined as the following formula. Examples of the calculation thereof are described in Chemical Reviews, Vol. 71, No. 6 (1971). In the present invention, the "log P" is a value determined at 25° C. through Chemical Compounds in Chemical Substance Control Law (4th edition) "Measurement of Partition Coefficient (1-octanol/water) of Chemical Substance <Part 1>" (published by The Chemical Daily).

$$\log P = \log([\text{substance}]_{Octanol}/[\text{substance}]_{Water})$$

(wherein $[\text{substance}]_{Octanol}$ represents a substance mole concentration in 1-octanol phase, and $[\text{substance}]_{Water}$ represents a substance mole concentration in aqueous phase)

Specific log P values of component (C) are benzyl alcohol (1.1), 2-benzyloxyethanol (1.2), 2-phenylethanol (1.2), 1-phneoxy-2-propanol (1.1), PPG-9 (0.9), propylene carbonate (−0.41), and γ-butyrolactone (−0.64).

Organic compounds of component (C) may be used singly or in combination of two or more species. From the viewpoint of imparting soft touch feeling to the treated hair, the component (C) content of the hair cosmetic composition of the present invention, relative to the total composition of the hair cosmetic composition, is 0.1 mass % or higher, preferably 0.2 mass % or higher, more preferably 0.4 mass % or higher, still more preferably 0.5 mass % or higher. From the viewpoint of ensuring sufficient effect for deforming the shape of hair, the component (C) content is lower than 20 mass %, preferably 17 mass % or lower, more preferably 15 mass % or lower, still more preferably 10 mass % or lower. In the case where the hair cosmetic composition is a multi-agent type hair cosmetic composition, component (c) may be contained in the first agent and/or the second agent. However, component (c) is preferably contained in the first agent and the second agent.

From the viewpoints of ensuring sufficient effect for deforming the shape of hair and imparting soft touch feeling to the treated hair, the ratio by mass of component (C) to the sum of components (A) and (B), (C)/[(A)+(B)], based on the total composition of the hair cosmetic composition, is preferably 0.001 or higher, more preferably 0.005 or higher, still more preferably 0.01 or higher, yet more preferably 0.02 or higher, and preferably lower than 1, more preferably 0.7 or lower, still more preferably 0.5 or lower, yet more preferably 0.3 or lower.

[Component (D): Water]

The medium of the hair cosmetic composition of the present invention is (D) water. In the case of the multi-agent type composition, each of the first agent, the second agent, and the like employs (D) water as the medium.

The hair cosmetic composition of the present invention may be a one-agent type composition or a multi-agent type (e.g., a two-agent type) composition. However, in order to enhance permeability of components (A) and (B) to hair to attain enhanced effects of the present invention, a multi-agent type composition in which component (A) and component (B) are contained in different agents and which is used in the format of successive application. Further, a two-agent type composition is more preferred. In a preferred mode of the successive application-type multi-agent type composition, components (B) and (D) are incorporated into the first agent, which is firstly applied to the hair, and components (A) and (D) are incorporated into the second agent, which is applied to the hair after application of the first agent. In this mode, component (C) may be incorporated into the first agent or the second agent. However, component (C) is more preferably incorporated into the first agent, and is further more preferably incorporated into both the first and second agents.

[pH]

The pH of the hair cosmetic composition of the present invention, in the case of a one-agent type composition, is preferably 4.0 or lower, more preferably 3.0 or lower, still more preferably 2.5 or lower, yet more preferably 2.0 or lower, from the viewpoint of permeability to hair, and preferably 1.0 or higher, more preferably 1.2 or higher, still more preferably 1.5 or higher, from the viewpoints of suppression of damage to the hair and irritation to the skin.

In the case of a multi-agent type composition, the pH of the agent containing component (A); i.e., the second agent, is preferably adjusted to fall within the aforementioned ranges. In the case of a multi-agent type composition, the pH of the agent containing component (B); i.e., the first agent, is preferably 6.0 or lower, more preferably 5.0 or lower, still more preferably 4.5 or lower, and preferably 2.5 or higher, more preferably 3.0 or higher, still more preferably 3.5 or higher, from the viewpoint of preventing discoloration of the composition. Notably, the pH of the hair cosmetic composition of the present invention refers to a pH value of a non-diluted or non-treated sample of the hair cosmetic composition measured at room temperature (25° C.) by means of a pH meter (model F-52, product of HORIBA).

In order to adjust the pH of the hair cosmetic composition to fall within the above ranges, a pH-adjusting agent may be appropriately used. Examples of the alkali pH-adjusting agent which may be used in the invention include ammonia and salts thereof; alkanolamines such as monoethanolamine, isopropanolamine, 2-amino-2-methylpropanol, and 2-aminobutanol, and salts thereof; alkane diamines such as 1,3-prpoanediamine, and salts thereof; carbonate salts such as guanidinium carbonate, sodium carbonate, potassium carbonate, sodium hydrogencarbonate, and potassium hydrogencarbonate; and hydroxides such as sodium hydroxide and potassium hydroxide. Examples of the acid pH-adjusting agent which may be used in the invention include inorganic acids such as hydrochloric acid and phosphoric acid; hydrochloric acid salts such as monoethanolamine hydrochloride; phosphate salts such as dihydrogen potassium phosphate and hydrogen disodium phosphate; organic acids other than component (A), such as lactic acid and malic acid.

[Other Components]

In order to improve touch feeling to treated hair for further enhancing the effects of the present invention, one or more compositions forming the hair cosmetic composition preferably contain a cationic surfactant. The cationic surfactant is preferably a quaternary mono-long-chain alkylammonium salt having one C8 to C24 alkyl group and three C1 to C4 alkyl groups.

Preferably, at least one quaternary mono-long-chain alkylammonium surfactant is selected from the compounds represented by the following formula:

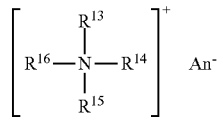

wherein $R^{13}$ represents a C8 to C22 saturated or unsaturated linear-chain or branched-chain alkyl group, $R^{17}$—CO—NH—$(CH_2)_m$—, or $R^{17}$—CO—O—$(CH_2)_m$— (wherein $R^{17}$ represents a C7 to C21 saturated or unsaturated linear-chain or branched-chain alky chain, and m is an integer of 1 to 4); $R^{14}$, $R^{15}$, and $R^{16}$ each represent a C1 to C4 alkyl group or a C1 to C4 hydroxylalkyl group; and $An^-$ represents a chloride ion, a bromide ion, a methosulfate ion, or an ethosulfate ion.

Examples of preferred cationic surfactants include quaternary long-chain ammonium compounds such as cetyltrimethylammonium chloride, myristyltrimethylammonium chloride, behenyltrimethylammonium chloride, cetyltrimethylammonium bromide, and stearamidopropyltrimonium chloride. These compounds may be used singly or as a mixture thereof.

The cationic surfactant content of the hair cosmetic composition of the present invention, relative to the total composition of the hair cosmetic composition, is preferably 0.05 mass % or higher, more preferably 0.1 mass % or higher, and preferably 10 mass % or lower, more preferably 5 mass % or lower. In the case where the hair cosmetic composition is a multi-agent type composition, the cationic surfactant may be contained in the first agent and/or the second agent.

For improving touch feeling of treated hair and hair manageability, the hair cosmetic composition of the present invention preferably contains a silicone. The silicone is preferably dimethylpolysiloxane or an amino-modified silicone.

As the aforementioned dimethylpolysiloxane, any of cyclic and acyclic dimethylpolysiloxane polymers may be used. Examples of the dimethylpolysiloxane include SH200 series, BY22-019, BY22-020, BY11-026, B22-029, BY22-034, BY22-050A, BY22-055, BY22-060, BY22-083, and FZ-4188 (products of Dow Corning Toray), and KF-9088, KM-900 series, MK-15H, and MK-88 (products of Shin-Etsu Chemical Co., Ltd.).

As the aforementioned amino-modified silicone, any silicones having an amino group or an ammonium group may be used. Examples thereof include an amino-modified silicone oil in which the total or a part of terminal hydroxyl groups are end-capped with a methyl group or the like, and a non-end-capped amodimethicone. Among them, compounds represented by the following formula:

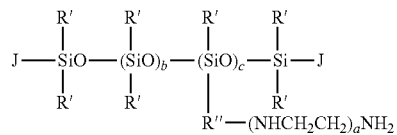

wherein R' represents a hydrogen atom, a hydroxyl group, or $R^Z$; $R^Z$ represents a substituted or non-substituted C1 to C20 monovalent hydrocarbon group; J represents $R^Z$, R''—$(NHCH_2CH_2)_aNH_2$, $OR^Z$, or a hydroxyl group; R'' represents C1 to C8 divalent hydrocarbon group; a is a number of 0 to 3; and b+c (number average) is 10 or greater and less than 20,000, preferably 20 or greater and less than 3,000, more preferably 30 or greater and less than 1,000, still more preferably 40 or greater and less than 800, may be used as preferred amino-modified silicones.

Specific examples of preferred amino-modified silicone commercial products include amino-modified silicone oils such as SF8452C and SS3551 (products of Dow Corning Toray), KF-8004, KF-867S, and KF-8015 (products of Shin-Etsu Chemical Co., Ltd.), and amodimethicone emulsions such as SM8704C, SM8904, BY22-079, FZ-4671, and FZ-4672 (products of Dow Corning Toray).

The silicone content of the hair cosmetic composition of the present invention, relative to the total composition of the hair cosmetic composition, is preferably 0.1 mass % or higher, more preferably 0.2 mass % or higher, still more preferably 0.5 mass % or higher, and preferably 20 mass % or lower, more preferably 10 mass % or lower, still more preferably 5 mass % or lower. In the case where the hair cosmetic composition is a multi-agent type composition, the silicone may be contained in the first agent and/or the second agent.

In order to improve hair touch feeling after the hair treatment, one or more component compositions forming the hair cosmetic composition preferably contain a cationic polymer.

In the present invention, the "cationic polymer" refers to a polymer having a cationic group or a group which can be ionized to form a cationic group, and an amphoteric polymer having a totally positive charge. Examples of the cationic polymer include an aqueous polymer having an amino group or an ammonium group in polymer side chains and an aqueous polymer formed of structural repeating units of quaternary diallylammonium salt. Specific examples include cationized cellulose derivatives, cationic starch, cationic guar gum derivatives, quaternary diallylammonium salt polymers and copolymers, and quaternarized polyvinylpyrrolidone derivatives. Among them, from the viewpoints of attaining effects (mild touch feeling during rinsing and shampooing, smoothness and easy finger passage, high hair manageability during drying, and moisturizing effect) and stability of the treatment agents, polymers formed of structural repeating units of quaternary diallylammonium salt, quaternarized polyvinylpyrrolidone derivatives, and cationized cellulose derivatives are preferred, with quaternary diallylammonium salt polymers and copolymers and cationized cellulose derivatives being more preferred.

Specific examples of preferred quaternary diallylammonium salt polymers and copolymers include dimethyldiallylammonium chloride polymer (Polyquaternium-6) (e.g., Merquat 100; product of Lubrizol Advanced Materials), dimethyldiallylammonium chloride-acrylic acid copolymer (Polyquaternium-22) (e.g., Merquat 280 or 295; products of Lubrizol Advanced Materials), and dimethyldiallylammonium chloride-acrylamide copolymer (Polyquaternium-7) (e.g., Merquat 550; product of Lubrizol Advanced Materials).

Specific examples of preferred quaternarized polyvinylpyrrolidone derivatives include a polymer produced through polymerization of a vinylpyrrolidone copolymer with dimethylaminoethyl methacrylate (Polyquaternium-11) (e.g., Gafquat 734, Gafquat 755, or Gafquat 755N (products of Ashland).

Specific examples of preferred cationized cellulose derivatives include a polymer formed through addition of glycidyltrimethylammonium chloride to hydroxycellulose (Polyquaternium-10) (e.g., Leogard G or GP (products of Lion Specialty Chemicals Co., Ltd.), or Polymer JR-125, JR-400, JR-30M, LR-400, or LR-30M (products of Amerchol), and hydroxyethylcellulose dimethyldiallylammonium chloride (Polyquaternium-4) (e.g., Cell coat H-100 or L-200 (products of Akzo Nobel).

The cationic polymer content of the hair cosmetic composition of the present invention, relative to the total composition of the hair cosmetic composition, is preferably 0.001 mass % or higher, more preferably 0.01 mass % or higher, still more preferably 0.05 mass % or higher, and preferably 20 mass % or lower, more preferably 10 mass % or lower. In the case where the hair cosmetic composition is a multi-agent type hair cosmetic composition, the cationic polymer may be contained in the first agent and/or the second agent.

Optionally, an antioxidant may be added to one or more components of the hair cosmetic composition. The type and amount of the antioxidant may be those generally employed in the art. An example thereof is ascorbic acid.

In addition to the aforementioned components, the hair cosmetic composition of the present invention may further contain other appropriate components which are generally employed in hair cosmetic compositions. However, the hair cosmetic composition of the present invention preferably contains substantially no precursor, which is incorporated into an oxidation hair dye, the dye dyeing hair via oxidation reaction between the precursor and a coupler. In other words, the hair cosmetic composition of the present invention substantially contains no aromatic compound having at least one amino group in which one amino group has another amino group or a hydroxyl group at an o-position or the p-position of the aromatic ring relative to the first amino group, and having a closed-shell quinoid structure after oxidation. Any compound of component (B) has a structure similar to that of resorcin, which is a typical coupler of an oxidation hair dye. However, a technical feature of the present invention resides in that component (A) and component (B) are polymerized in hair shafts, whereby hair shape can be changed as desired through post heat treatment. Thus, the technical concept of the present invention completely differs from use of resorcin in an oxidation hair dye.

Also, the technical concept of the hair cosmetic composition of the present invention differs from the technique disclosed in Patent Document 3; i.e., formation of an oligomer of glycerylaldehyde and resorcin in the presence of boric acid or silicic acid. Thus, preferably, the composition of the present invention substantially contains no boric acid or silicic acid.

Yet preferably, the hair cosmetic composition of the present invention contains substantially no hair reducing agent. A characteristic feature of the present invention is to realize hair deforming not through breakage of S—S bonds of a protein in hair shafts. Therefore, the present invention absolutely differs from a permanent wave agent which breaks S—S bonds of hair shafts by the action of a reducing agent. Examples of the hair reducing agent include thiols such as thioglycolic acid, dithioglycolic acid, cysteine, acetylcysteine, and butyrolactone thiol, hydrogen sulfite, and a salt thereof.

In the present specification, the expression "substantially containing no specific compound" or an equivalent expression refers to the hair cosmetic composition having a target compound content, relative to the total composition of the hair cosmetic composition, of preferably less than 0.1 mass %, more preferably less than 0.01 mass %. Yet more preferably, the hair cosmetic composition contains no target compound.

The hair cosmetic composition of the present invention is highly safe to the human body and gives less damage to hair. Thus, the composition can be suitably applied particularly to human hair.

[Hair Deforming Treatment Method]

The method for the treatment of hair, realizing semi-permanent or permanent deforming of hair and employing the hair cosmetic composition of the present invention, may be carried out through a hair treatment method comprising the following steps (i) and (ii). Notably, the term "hair cosmetic composition" in the description in relation to the hair treatment refers to a composition actually applied to hair and encompasses any of a one-agent type hair cosmetic composition, a single application-type multi-agent type hair cosmetic composition which is a mixture of a first agent and a second agent, and a successive application-type multi-agent type hair cosmetic composition employing a first agent and a second agent.

The case of a one-agent type hair cosmetic composition:

(i) a step of applying a one-agent type hair cosmetic composition to hair; and (ii) a step of heating and shaping the hair to which the hair cosmetic composition is applied.

The case of a multi-agent type hair cosmetic composition in a single application format:

(i) a step of mixing a first agent and a second agent of a multi-agent type hair cosmetic composition and applying the obtained hair cosmetic composition to hair; and (ii) a step of shaping the hair to which the hair cosmetic composition has been applied, by heating.

The case of a multi-agent type hair cosmetic composition in a successive application format:

(i) a step of applying a first agent of a multi-agent type hair cosmetic composition to hair and then applying a second agent of the composition to the first agent applied onto the hair; and (ii) a step of heating and shaping the hair to which the hair cosmetic composition is applied.

In step (i), the hair cosmetic composition may be applied to dry hair or wet hair. However, the target hair is preferably wetted with water before step (i) so as to swell the hair and promote permeation of the hair cosmetic composition to the hair. The relative mass of the hair cosmetic composition applied to hair in step (i); i.e., the mass ratio of liquid to hair (mass of hair cosmetic composition/mass of hair) is preferably 0.05 or higher, more preferably 0.1 or higher, still more preferably 0.25 or higher, yet more preferably 0.5 or higher, and preferably 5 or lower, more preferably 3 or lower, still more preferably 2 or lower. In the case of the successive application-type multi-agent type hair cosmetic composition, from the viewpoint of applicability, each of the first agent and the second agent preferably satisfies the above liquid-to-hair conditions. The target hair may be the total hair or a part of the hair.

In step (i), when the successive application-type multi-agent type hair cosmetic composition is used, the first agent is firstly applied. In order to promote permeation of the hair cosmetic composition and enhance the effects of the invention, the hair to which the first agent of the hair cosmetic composition has been applied may be allowed to stand for a certain period of time, and then the second agent may be further applied thereto. For suitably causing the hair cosmetic composition to permeate and diffuse in hair, the time of allowing to stand is preferably 1 minute or longer, more preferably 3 minutes or longer, still more preferably 5 minutes or longer, and preferably 1 hour or shorter, more preferably 30 minutes or shorter, still more preferably 20 minutes or shorter. In this case, in order to promote permeation of the first agent, the hair may be heated. The heating temperature is preferably 40 to 90° C.

In step (i), when the successive application-type multi-agent type hair cosmetic composition is used, a step of washing of the first agent (hereinafter may be referred to as an "intermediate rinsing step") may be performed after application and staying of the first agent and before application of the second agent. From the viewpoint of shortening the total treatment time, the treatment method preferably includes no intermediate rinsing step. When no intermediate rinsing step is included, the molecular weight of component (B) contained in the first agent is preferably 100 to 180, more preferably 100 to 140, for further enhancing the effect for deforming the shape of hair. In contrast, from the viewpoint of enhancing touch feeling after hair deforming treatment, the treatment method preferably includes an intermediate rinsing step. When an intermediate rinsing step is included, the molecular weight of component (B) contained in the first agent is preferably 140 to 1,000, more preferably 180 to 1,000, for further enhancing the effect for deforming the shape of hair and attaining favorable touch feeling after hair deforming.

Also, when the successive application-type multi-agent type hair cosmetic composition is used, no particular limitation is imposed on the amounts of the first and second agents applied to hair. The molar ratio of component (B) to component (A) applied to hair, (B)/(A), is preferably 0.001 or higher, more preferably 0.1 or higher, still more preferably 0.2 or higher, and yet more preferably 0.25 or higher, and preferably lower than 2.5, more preferably 2.3 or lower, still more preferably 2.0 or lower, yet more preferably 1.5 or lower, in application of the hair cosmetic composition. In the present specification, each of the amounts of components (A) and (B) applied to hair is calculated from the amount of the first agent or the second agent applied to the hair, and the component (A) content or component (B) content of the first agent or the second agent.

An optional step of allowing the hair to which the hair cosmetic composition has been applied to stand for a specific period of time may be included between step (i) and step (ii). In this case, for suitably causing the hair cosmetic composition to permeate and diffuse in hair, the time of allowing to stand is preferably 1 minute or longer, more preferably 3 minutes or longer, still more preferably 5 minutes or longer, and preferably 1 hour or shorter, more preferably 30 minutes or shorter, still more preferably 20 minutes or shorter.

In the step of allowing the hair to stand, the hair may be heated for promoting permeation of the hair cosmetic composition. When heating is performed, the heating temperature is preferably 40 to 90° C. Though heating, a low-molecular-weight oligomer can be polymerized in hair shafts before step (ii). Thus, step (ii) can be performed more advantageously, which is preferred.

Between step (i) and step (ii), the hair to which the hair cosmetic composition has been applied may or may not be rinsed. However, no rinsing is preferably performed. In this case, the effects of sufficiently retaining components of the hair cosmetic composition in hair, imparting a semi-permanent shape to hair, and semi-permanently re-deforming the hair by heating can be further ensured.

For imparting a semi-permanent shape to hair and semi-permanently re-deforming the deformed hair by heat, the heating temperature in step (ii) is preferably 50° C. or higher, more preferably 60° C. or higher, still more preferably 80° C. or higher. In order to suppress rapid evaporation of water during heating, the heating temperature is preferably 250° C. or lower, more preferably 240° C. or lower, still more preferably 230° C. or lower. Examples of the heating means include a hair iron, an electrically heating rod, and a hot curler.

The heating time in step (ii) is appropriately adjusted in accordance with the apparatus and temperature employed in step (ii). However, in order to permeate and diffuse the hair cosmetic composition in hair shafts to induce satisfactory polymerization, the heating time is preferably 1 second or longer, more preferably 5 seconds or longer, still more preferably 1 minute or longer, yet more preferably 5 minutes or longer, further more preferably 15 minutes or longer, further more preferably 30 minutes or longer. From the viewpoint of suppression of damage to hair, the heating time is preferably 2 hours or shorter, more preferably 1 hour or shorter, still more preferably 45 minutes or shorter.

The shaping performed in step (ii) encompasses straightening and curling. Examples of the straightening method include blow-heating the hair by means of a hair drier, while drawing the hair by means of a tool such as the hand, a comb, or a brush, and heating the hair by means of a hair iron. From the viewpoint easiness of shaping, a hair iron is preferably employed. In one mode of straightening the hair by heating with a hair iron, the hair is nipped by a flat iron, and the flat iron is caused to slide from hair roots to hair ends. In another mode, the hair is nipped by a flat iron, while drawing the hair by means of a tool such as the hand, a comb, or a brush, and the hair is maintained in that state. Needless to say, the two modes may be combined. In curling the hair, examples of the curling method include heating the hair which is wound by electrically heating rods, a hot curler, or the like for a certain period of time, and winding the hair by a curl iron for a certain period of time.

Preferably, step (ii) is performed under the conditions where rapid water evaporation is suppressed. Specific means for suppressing evaporation of water include wrapping the hair to which the hair cosmetic composition has been applied with a plastic film (e.g., a food wrapping film), a cap, or the like, and continuously spraying steam (e.g., superheated steam) to the hair.

After carrying out step (ii), the shaped hair may or may not be rinsed. However, rinsing is preferably performed so as to prevent impairment hair touch feeling due to remaining polymers.

(Hair Re-Deforming Method)

After the hair has been deformed through a method including step (i) or (ii), the deformed hair may be subjected to a step of semi-permanently deforming the hair to a different shape by heating (i.e., a re-deforming step). The heating temperature in re-deforming is preferably 30° C. or higher, more preferably 40° C. or higher, and preferably 230° C. or lower, more preferably 220° C. or lower, still more preferably 210° C. or lower. In the re-deforming of hair, application of the hair cosmetic composition of the present invention, a hair treatment agent containing a reducing agent (e.g., a permanent agent), or another type of hair treatment agent such as an alkali relaxer is preferably omitted.

Hereinafter, specific procedures of a step of semi-permanently deforming the hair to a different shape by heating will be described.

Re-Deforming of Shaped Curly Hair to Straight Hair

Examples of the method of re-deforming shaped curly hair to straight hair include blow-heating the hair by means of a hair drier, while drawing the hair by means of a tool such as the hand, a comb, or a brush, and heating the hair by means of a hair iron. From the viewpoint easiness of hair deforming, a hair iron is preferably employed. In one procedure of straightening the hair by heating with a hair iron, the hair is nipped by a hair iron, and the hair iron is caused to slide from hair roots to hair ends. In another procedure, the hair is nipped by a hair iron, while drawing the hair by means of a tool such as the hand, a comb, or a brush, and the hair is maintained in that state. The two procedures may be combined.

Under any conditions, including the type of the hair iron, the material of heating members thereof, the heating temperature employed, and the mode of operating the hair iron, in order to attain semi-permanent or permanent hair deforming, the actual temperature (hair temperature) during heating of the hair is preferably 120° C. or higher, more preferably 150° C. or higher. From the viewpoints of prevention of hair damage and deforming hair semi-permanently or permanently, the temperature is preferably 230° C. or lower, more preferably 220° C. or lower, still more preferably 210° C. or lower.

The temperature of heating hair can be monitored by means of, for example, a radiation thermometer (model ST653, product of SENTRY).

Re-Deforming of Straightened Hair to Curly Hair

Examples of the method of deforming straightened hair to curly hair include heating the hair which is wound by heating rods, a hot curler, or the like for a certain period of time, and winding the hair by a curl iron for a certain period of time.

In the re-deforming method, the actual temperature (hair temperature) during heating of the hair is preferably 30° C. or higher, more preferably 40° C. or higher, in order to suitably deforming the hair permanently or semi-permanently. From the viewpoints of prevention of hair damage and deforming hair semi-permanently or permanently, the temperature is preferably 180° C. or lower, more preferably 120° C. or lower, still more preferably 100° C. or lower, yet more preferably 80° C. or lower, further more preferably 60° C. or lower.

In re-deforming of hair, heating may be performed when the hair is dry or after the hair has been wetted with water. From the viewpoint of deforming hair semi-permanently or permanently, heating is preferably performed after the hair has been wetted with water.

The time of heating hair in hair re-deforming may be appropriately tuned in accordance with the heating tool, heating temperature, and other conditions employed in heating. From the viewpoint of deforming hair semi-permanently or permanently, the heating time is preferably 1 second or longer, more preferably 5 seconds or longer, still more preferably 1 minute or longer, yet more preferably 5 minutes or longer, further more preferably 15 minutes or longer, further more preferably 30 minutes or longer. In order to prevent hair damage, the heating time is preferably 2 hours or shorter, more preferably 1 hour or shorter, still more preferably 45 minutes or shorter.

The hair treatment method which can shape hair semi-permanently or permanently is not particularly limited to some embodiments. Preferred hair treatment methods include the following three embodiments (patterns).

Pattern 1: A case of one-agent type hair cosmetic composition 1) optionally wetting hair with water;

2) applying, to the hair, the hair cosmetic composition of the present invention containing the following components (A) to (D):

component (A): one or more compounds selected from the group consisting of glyoxylic acid, a glyoxylic acid hydrate, a glyoxylate salt, and a glyoxylamide;

component (B): a phenolic compound having an electron-donating group on at least one m-position and having a hydrogen atom on at least one of the o-positions and the p-position, wherein the electron-donating group on the m-position may form, together with an adjacent carbon atom, a benzene ring optionally substituted with hydroxyl group(s);

component (C): organic solvent having a boiling point of 100° C. or higher at 1,013.25 hPa; and component (D): water;

3) optionally allowing the hair to which the hair cosmetic composition has been applied to stand for 1 minute or more and 1 hour or less, wherein the hair may optionally be heated at 40 to 90° C.;

4) heating and shaping the hair at 50 to 250° C.;

5) optionally rinsing the hair;

6) optionally heating and reshaping the hair at 40 to 230° C.; and 7) optionally heating and further shaping the re-deformed hair at 40 to 230° C.

Pattern 2: A case of single application multi-agent type hair cosmetic composition 1) optionally wetting hair with water;
2) applying, to the hair, the hair cosmetic composition of the present invention containing the following components (A) to (D):
    component (A): one or more compounds selected from the group consisting of glyoxylic acid, a glyoxylic acid hydrate, a glyoxylate salt, and a glyoxylamide;
    component (B): a phenolic compound having an electron-donating group on at least one m-position and having a hydrogen atom on at least one of the o-positions and the p-position, wherein the electron-donating group on the m-position may form, together with an adjacent carbon atom, a benzene ring optionally substituted with hydroxyl group(s);
    component (C): organic solvent having a boiling point of 100° C. or higher at 1,013.25 hPa; and
    component (D): water, wherein the composition is prepared by mixing a first agent containing the components (B) and (D) and preferably containing component (C), with a second agent preferably containing component (C) (wherein the component (C) is essentially contained in at least one of the first and second agents);
3) optionally allowing the hair to which the hair cosmetic composition has been applied to stand for 1 minute or more and 1 hour or less, wherein the hair may optionally be heated at 40 to 90° C.;
4) heating and shaping the hair at 50 to 250° C.;
5) optionally rinsing the hair;
6) optionally heating and reshaping the hair at 40 to 230° C.; and
7) optionally heating and further shaping the re-deformed hair at 40 to 230° C.

Pattern 3: A Case of Successive Application Multi-Agent Type Hair Cosmetic Composition 1) optionally wetting hair with water;
2) applying, to hair, a first agent containing the following components (B) and (D), and preferably additionally containing component (C) (wherein the component (C) is essentially contained in at least one of the first and second agents):
    component (B): a phenolic compound having an electron-donating group on at least one m-position and having a hydrogen atom on at least one of the o-positions and the p-position, wherein the electron-donating group on the m-position may form, together with an adjacent carbon atom, a benzene ring optionally substituted with hydroxyl group(s);
    component (C): organic solvent having a boiling point of 100° C. or higher at 1,013.25 hPa; and
    component (D): water;
3) optionally allowing the hair to which the hair cosmetic composition has been applied to stand for 1 minute or more and 1 hour or less, wherein the hair may optionally be heated at 40 to 90° C.;
4) optionally rinsing off the first agent remaining on the hair;
5) further applying, to a portion of the hair to which the first agent has been applied, a second agent containing the following components (A) and (D), and preferably additionally containing component (C):
    component (A): one or more compounds selected from the group consisting of glyoxylic acid, a glyoxylic acid hydrate, a glyoxylate salt, and a glyoxylamide;
    component (C): organic solvent having a boiling point of 100° C. or higher at 1,013.25 hPa; and
    component (D): water;
6) optionally allowing the hair to which the hair cosmetic composition has been applied to stand for 1 minute or more and 1 hour or less, wherein the hair may optionally be heated at 40 to 90° C.;
7) heating and shaping the hair at 50 to 250° C.;
8) optionally rinsing the hair;
9) optionally heating and reshaping the hair at 40 to 230° C.; and
10) optionally heating and further shaping the re-deformed hair at 40 to 230° C.

The technical feature of the hair treatment method of the present invention completely differs from conventional techniques such as a permanent treatment by use of a reducing agent and a relaxation treatment by use of a strong-alkali hair treatment agent having a pH of 12 to 14, and can shape hair to a form as desired. Thus, the hair treatment method of the present invention does not include a step of applying, to hair, a hair treatment agent containing a reducing agent or a strong-alkali hair treatment agent having a pH of 12 to 14. Therefore, as compared with conventional hair deforming methods, the hair treatment method according to the present invention is advantageous in that the hair can be deformed without damaging the hair.

In relation to the aforementioned embodiments, there will next be disclosed more preferred embodiments of the present invention.

<1>

A hair cosmetic composition, which is a one-agent type hair cosmetic composition composed of a single agent, or a multi-agent type hair cosmetic composition composed of multiple agents, wherein the hair cosmetic composition totally comprising the following components (A) to (D), the component (C) content, relative to the total composition of the hair cosmetic composition, being 0.1 mass % or higher and lower than 20 mass %:

(A): one or more compounds selected from the group consisting of glyoxylic acid, a glyoxylic acid hydrate, a glyoxylate salt, and a glyoxylamide;

(B): a phenolic compound having an electron-donating group on at least one m-position, preferably two or three positions, and having a hydrogen atom on at least one of the o-positions and the p-position, wherein the electron-donating group on the m-position may form, together with an adjacent carbon atom, a benzene ring optionally substituted with hydroxyl group(s);

(C): organic solvent having a boiling point of 100° C. or higher at 1,013.25 hPa; and (D): water.

<2>

The hair cosmetic composition as described in <1> above, wherein the molar ratio of component (B) to component (A), (B)/(A), of applied to hair is preferably 0.001 or higher, more preferably 0.1 or higher, still more preferably 0.2 or higher, yet more preferably 0.25 or higher, and preferably lower than 2.5, more preferably 2.3 or lower, still more preferably 2.1 or lower, yet more preferably 1.9 or lower, further more preferably 1.7 or lower, further more preferably 1.6 or lower.

<3>

The hair cosmetic composition as described in <1> or <2> above, wherein component (C) is preferably at least one compound selected from the group consisting of the following compounds (c1) through (c5).

(c1) Compounds represented by formula (3)

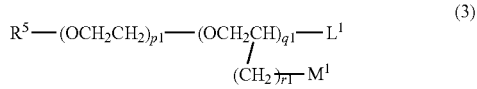

(wherein $R^5$ represents a group $R^6$-Ph-$R^7$— (wherein $R^6$ represents a hydrogen atom, a methyl group, or a methoxy group; $R^7$ represents a chemical bond or a C1 to C3 saturated or unsaturated divalent hydrocarbon group; and Ph represents a p-phenylene group); $L^1$ and $M^1$ each represent a hydrogen atom or a hydroxyl group; and each of $p^1$, $q^1$, and $r^1$ is an integer of 0 to 5, wherein, in the case of $p^1=q^1=0$, $L^1$ is a hydroxyl group, and $R^5$ is not a group $R^6$-Ph-)

(c2) Compounds represented by formula (4)

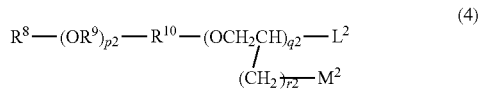

(wherein $R^8$ represents a hydrogen atom or a C1 to C12 linear-chain or branched-chain alkyl group; $R^9$ represents a C1 to C10 linear-chain or branched-chain saturated divalent hydrocarbon group optionally substituted with one hydroxyl group; $R^{10}$ represents a chemical bond or a C1 to C5 linear-chain or branched-chain divalent saturated hydrocarbon group optionally substituted with one $[CH_2CH(Q)O]_s$ (wherein Q represents a hydrogen atom or a methyl group, and s is an integer of 1 to 20); $L^2$ represents a hydrogen atom, a hydroxyl group, a C1 to C10 linear-chain or branched-chain alkoxy group or a phenoxy group; $M^2$ represents a hydrogen atom or a hydroxyl group; each of $p^2$ and $q^2$ is an integer of 0 to 20; and $r^2$ is an integer of 0 to 10)

(c3) N-alkyl- or N-alkenylpyrrolidones in which a C1 to C18 alkyl or alkenyl group is bonded to the nitrogen atom (c4) C3 or C4 alkylene carbonates optionally substituted with hydroxyl group(s)

(c5) Lactones or cyclic ketones represented by formula (5), (6), or (7)

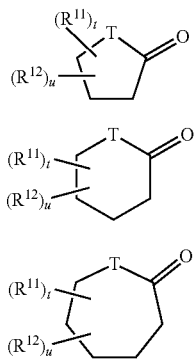

(wherein T represents a methylene group or an oxygen atom; $R^{11}$ and $R^{12}$ are substituents which are different from each other; and each of t and u is 0 or 1)

<4>
The hair cosmetic composition as described in any one of <1> to <3> above, wherein the octanol-water partition coefficient (log P) of component (C) at 25° C. is preferably lower than 10, more preferably 3 or lower, still more preferably 2 or lower, and preferably −2 or higher, more preferably −1 or higher.

<5>
The hair cosmetic composition as described in any one of <1> to <4> above, wherein component (C) is preferably at least one compound selected from the group consisting of benzyl alcohol, phenoxyethanol, 1,2-butanediol, dipropylene glycol, glycerin, PEG-8, PPG-9, propylene glycol, and ethylhexyl glycerin.

<6>
The hair cosmetic composition as described in any one of <1> to <5> above, wherein the component (A) content, relative to the total composition of the hair cosmetic composition and in terms of glyoxylic acid, is preferably 1 mass % or higher, more preferably 2.0 mass % or higher, still more preferably 2.5 mass % or higher, yet more preferably 3.0 mass % or higher, and preferably 30 mass % or lower, more preferably 25 mass % or lower, still more preferably 20 mass % or lower, yet more preferably 15 mass % or lower, further more preferably 12 mass % or lower.

<6>
The hair cosmetic composition as described in any one of <1> to <5> above, wherein the component (B) content, relative to the total composition of the hair cosmetic composition, is preferably 0.2 mass % or higher, more preferably 0.5 mass % or higher, still more preferably 1.0 mass % or higher, yet more preferably 1.5 mass % or higher, and preferably 40 mass % or lower, more preferably 30 mass % or lower, still more preferably 25 mass % or lower, yet more preferably 23 mass % or lower, further more preferably 20 mass % or lower.

<7>
The hair cosmetic composition as described in any one of <1> to <6> above, wherein the component (C) content, relative to the total composition of the hair cosmetic composition, is preferably 0.2 mass % or higher, more preferably 0.4 mass % or higher, still more preferably 0.5 mass % or higher, and preferably 17 mass % or lower, more preferably 15 mass % or lower, still more preferably 10 mass % or lower.

<8>
The hair cosmetic composition as described in any one of <1> to <7> above, wherein component (B) is preferably resorcin (B1).

<9>
The hair cosmetic composition as described in <8> above, wherein the component (B1) content, relative to the total composition of the hair cosmetic composition, is preferably 0.2 mass % or higher, more preferably 0.5 mass % or higher, still more preferably 1.0 mass % or higher, yet more preferably 1.5 mass % or higher, further more preferably 2 mass % or higher, further more preferably 3 mass % or higher, further more preferably 4 mass % or higher, further more preferably 5 mass % or higher, and preferably 40 mass % or lower, more preferably 30 mass % or lower, still more preferably 25 mass % or lower, yet more preferably 23 mass % or lower, further more preferably 20 mass % or lower, further more preferably 17 mass % or lower.

<10>
The hair cosmetic composition as described in <8> or <9> above, wherein the molar ratio of component (B1) to component (A), (B1)/(A), of the hair cosmetic composition applied to hair is preferably 0.2 or higher, more preferably 0.3 or higher, still more preferably 0.4 or higher, yet more preferably 0.5 or higher, further more preferably 0.7 or higher, and preferably lower than 2.5, more preferably 2.3 or lower, still more preferably 2.0 or lower, yet more preferably 1.5 or lower, further more preferably 1.2 or lower.

<11>

The hair cosmetic composition as described in any one of <1> to <7> above, wherein component (B) is preferably one or more compounds (B2) represented by the following formula (1):

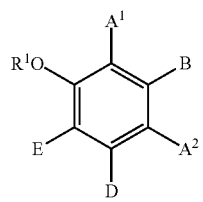
(1)

(wherein:

$R^1$ represents a hydrogen atom or a methyl group;

$A^1$ and $A^2$, which may be identical to or different from each other, each represent a hydrogen atom, a C1 to C12 linear-chain or branched-chain alkyl or alkenyl group, an optionally substituted C7 to C12 aralkyl or arylalkenyl group, a C1 to C6 linear-chain or branched-chain alkoxy or alkenyloxy group, a halogen atom, or —CO—$R^2$ (wherein $R^2$ represents a C1 to C12 linear-chain or branched-chain alkyl or alkenyl group, an optionally substituted C7 to C12 aralkyl or arylalkenyl group, or an optionally substituted C6 to C12 aromatic hydrocarbon group);

B represents a hydrogen atom, a C1 to C12 linear-chain or branched-chain alkyl or alkenyl group, an optionally substituted C7 to C12 aralkyl or arylalkenyl group, or —$OR^3$ or —$COOR^3$ (wherein $R^3$ represents a hydrogen atom or a C1 to C6 linear-chain or branched-chain alkyl or alkenyl group);

D represents a hydrogen atom, a hydroxyl group, a methyl group, or a C1 to C12 linear-chain or branched-chain alkoxy or alkenyloxy group; and E represents a hydrogen atom, a hydroxyl group, a C1 to C6 linear-chain or branched-chain alkyl or alkenyl group, or a C1 to C6 linear-chain or branched-chain alkoxy or alkenyloxy group, wherein two or three of $A^1$, $A^2$, B, and E each are a hydrogen atom, with each of remaining being a group which is not a sulfo group, and in the case where D is a hydrogen atom or a methyl group, $A^1$ and B, or $A^2$ and B form an optionally hydroxyl group-substituted benzene ring with two adjacent carbon atoms), more preferably compounds represented by the following formula (1-1), (1-2), (1-3-a), or (1-3-b):

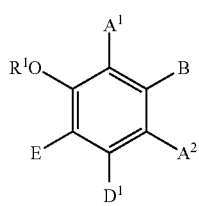
(1-1)

wherein $R^1$, $A^1$, $A^2$, B, and E are defined as above, and $D^1$ represents a hydroxyl group or a methoxy group;

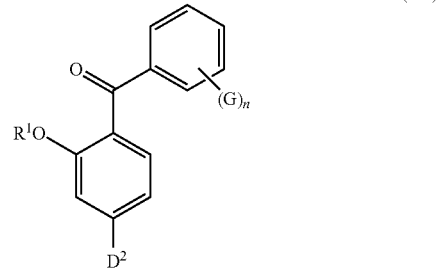
(1-2)

wherein $R^1$ has the same meaning as defined above; $D^2$ represents a hydroxyl group or a C1 to C12 alkoxy group; G represents a hydroxyl group, a C1 to C6 linear-chain or branched-chain alkyl or alkenyl group, or a C1 to C6 alkoxy group; and n is an integer of 0 to 2;

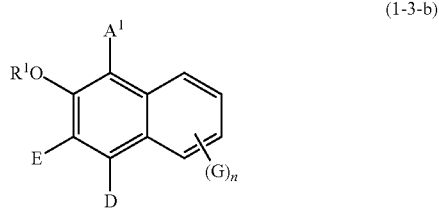
(1-3-a)

wherein $R^1$, $A^2$, E, D, G, and n are defined as above; or

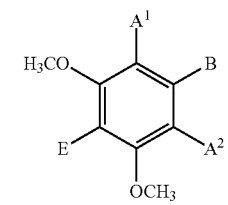
(1-3-b)

wherein $R^1$, $A^1$, E, D, G, and n are defined as above, more preferably one or more compounds represented by formula (1-1-1), (1-1-2), or (1-1-3):

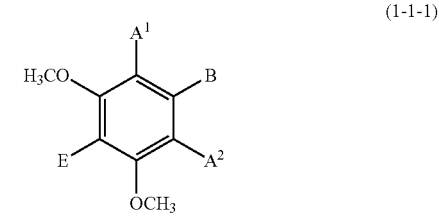
(1-1-1)

wherein $A^1$, $A^2$, B, and E are defined as above;

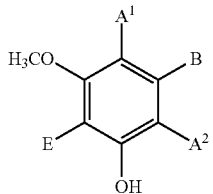
(1-1-2)

wherein $A^1$, $A^2$, B, and E are defined as above; or

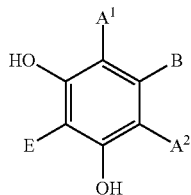
(1-1-3)

wherein $A^1$, $A^2$, B, and E are defined as above.

<12>

The hair cosmetic composition as described in <11> above, wherein component (B2) is preferably one or more species selected from the group consisting of 2-methylresorcin, 4-chlororesorcin, 4-alkylresorcin, 4-aralkylresorcin, 4-acylated resorcin, 5-alkylresorcin, 5-aralkylresorcin, 5-hydroxyarylalkenylresorcin, 2,4,6-trihydroxyphenylaralkylketone, gallic acid, and a gallate ester; more preferably 4-butylresorcin (trivial name: rucinol), 4-(1-phenylethyl)resorcin (trivial name: Symwhite 377), 5-(hydroxyphenylethenyl)resorcin (trivial name: resveratrol), 3-hydroxyphenyl-1-(benzene-2,4,6-triol)propan-1-one (trivial name: phloretin), 4-(2,4-dihydroxybenzoyl)resorcin (trivial name: Benzophenone-2), 5-(hydroxyphenylethenyl)-1,3-dimethoxybenzene (trivial name: pterostilbene), and 1-naphthol; still more preferably 2-methylresorcin, 4-chlororesorcin, 1-naphthol, 4-n-butylresorcinol, 4-phenylresorcinol, 5-(hydroxyphenylethenyl)resorcin, 3-hydroxyphenyl-1-(benzene-2,4,6-triol)propan-1-one, and 4-(2,4-dihydroxybenzoyl)resorcin.

<13>

The hair cosmetic composition as described in <11> or <12> above, wherein the component (B2) content, relative to the total hair cosmetic composition, is preferably 0.2 mass % or higher, more preferably 0.5 mass % or higher, still more preferably 1.0 mass % or higher, yet more preferably 1.5 mass % or higher, further more preferably 2 mass % or higher, and from the viewpoint of easiness in mixing components, preferably 40 mass % or lower, more preferably 30 mass % or lower, still more preferably 25 mass % or lower, yet more preferably 23 mass % or lower, further more preferably 20 mass % or lower, further more preferably 17 mass % or lower, further more preferably 15 mass % or lower, further more preferably 12 mass % or lower.

<14>

The hair cosmetic composition as described in any one of <11> to <13> above, wherein the molar ratio of component (B2) to component (A), (B2)/(A), of the hair cosmetic composition applied to hair is preferably 0.001 or higher, more preferably 0.1 or higher, still more preferably 0.2 or higher, yet more preferably 0.25 or higher, and preferably lower than 2.5, more preferably 2.3 or lower, still more preferably 2.0 or lower, yet more preferably 1.5 or lower, further more preferably 1.2 or lower.

<15>

The hair cosmetic composition as described in any one of <1> to <7> above, wherein component (B) is preferably one or more compounds (B3) represented by the following formula (2):

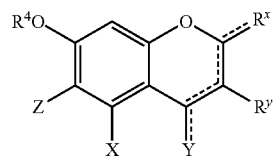
(2)

wherein, $R^4$ represents a hydrogen atom or a methyl group;

X represents a hydrogen atom, a hydroxyl group, or a methoxy group;

Y represents a hydrogen atom, an oxygen atom, a hydroxyl group, or a methoxy group;

Z represents a hydrogen atom or a C1 to C5 linear-chain or branched-chain alkyl or alkenyl group;

$R^x$ represents a hydrogen atom, an oxygen atom, a hydroxyl group, a methoxy group, or an aromatic hydrocarbon group which may be substituted with 1 to 3 hydroxyl groups or methoxy groups and which optionally forms a condensed ring with 1,3-dioxolane;

$R^y$ represents a hydrogen atom, a hydroxyl group, a methoxy group, an aromatic hydrocarbon group which may be substituted with 1 to 3 hydroxyl groups or methoxy groups and which optionally forms a condensed ring with 1,3-dioxolane, or an arylcarbonyloxy or aralkylcarbonyloxy group which may be substituted with 1 to 3 hydroxyl groups or methoxy groups;

a dotted line portion may be a double bond;

each of the combinations of the dotted line and the solid line being adjacent to $R^x$ or Y denotes a double bond in the case where $R^x$ or Y is an oxygen atom, and denotes a single bond in the other cases; and Z represents a C1 to C5 linear-chain or branched-chain alkyl or alkenyl group, only when $R^x$ or $R^y$ is an o,p-dihydroxyaromatic hydrocarbon group, and represents a hydrogen atom in the other cases, more preferably one or more compounds represented by the following formula (2-1), (2-2), (2-3), (2-4), or (2-5);

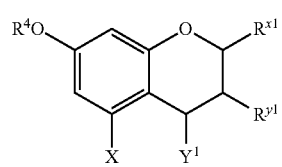
(2-1)

$R^4$ and X are defined as above;

$Y^1$ represents a hydrogen atom, a hydroxyl group, or a methoxy group;

$R^{x1}$ represents an aromatic hydrocarbon group which may be substituted with 1 to 3 hydroxyl groups or methoxy groups and which optionally forms a condensed ring with 1,3-dioxolane; and $R^{y1}$ represents a hydrogen atom, a hydroxyl group, a methoxy group, an aromatic hydrocarbon group which may be substituted with 1 to 3 hydroxyl groups or methoxy groups and which optionally forms a condensed ring with 1,3-dioxolane, or an arylcarbonyloxy or aralkylcarbonyloxy group which may be substituted with 1 to 3 hydroxyl groups or methoxy groups;

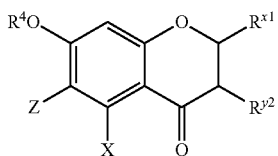

(2-2)

wherein $R^4$, X, Z, and $R^{x1}$ are defined as above, and $R^{y2}$ represents a hydrogen atom, a hydroxyl group, or a methoxy group; and Z represents a C1 to C5 linear-chain or branched-chain alkyl or alkenyl group, only when $R^{x1}$ is an o,p-dihydroxyaromatic hydrocarbon group, and represents a hydrogen atom in the other cases;

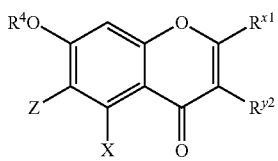

(2-3)

wherein $R^4$, X, Z, $R^{x1}$, and $R^{y2}$ are defined as above, and

Z is a C1 to C5 linear-chain or branched-chain alkyl or alkenyl group, only when $R^{x1}$ is an o,p-dihydroxyaromatic hydrocarbon group. In the other cases, Z is a hydrogen atom;

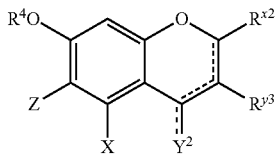

(2-4)

wherein $R^4$, X, Z, and the dotted line are defined as above;

$Y^2$ represents a hydrogen atom or an oxygen atom;

$R^{x2}$ represents a hydrogen atom, a hydroxyl group, or a methoxy group;

$R^{y3}$ represents an aromatic hydrocarbon group which may be substituted with 1 to 3 hydroxyl groups or methoxy groups and which optionally forms a condensed ring with 1,3-dioxolane;

the combination of the dotted line and the solid line being adjacent to $Y^2$ denotes a double bond in the case where $Y^2$ is an oxygen atom, and denotes a single bond in the other cases; and Z represents a C1 to C5 linear-chain or branched-chain alkyl or alkenyl group, only when $R^{y3}$ is an o,p-dihydroxyaromatic hydrocarbon group, and represents a hydrogen atom in the other cases; or

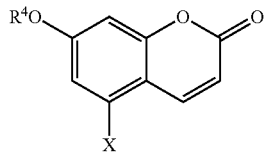

(2-5)

wherein $R^4$ and X are defined as above.

<16>

The hair cosmetic composition as described in <15> above, wherein component (B3) is preferably one or more compounds selected from the group consisting of catechin, epicatechin, epigallocatechin, catechin gallate, epicatechin gallate, epigallocatechin gallate, quercetin, morin, hesperetin, naringenin, chrysin, daidzein, equol, and umbelliferone.

<17>

The hair cosmetic composition as described in <15> or <16> above, wherein the component (B3) content, relative to the total hair cosmetic composition, is preferably 0.2 mass % or higher, more preferably 0.5 mass % or higher, still more preferably 1.0 mass % or higher, yet more preferably 1.5 mass % or higher, and from the viewpoint of suitably mixing components, preferably 40 mass % or lower, more preferably 30 mass % or lower, still more preferably 25 mass % or lower, yet more preferably 23 mass % or lower, further more preferably 20 mass % or lower, further more preferably 17 mass % or lower further more preferably 15 mass % or lower, further more preferably 12 mass % or lower.

<18>

The hair cosmetic composition as described in any one of <15> to <17> above, wherein the molar ratio of component (B3) to component (A), (B3)/(A), of the hair cosmetic composition applied to hair is preferably 0.001 or higher, more preferably 0.1 or higher, still more preferably 0.2 or higher, yet more preferably 0.25 or higher, and preferably lower than 2.5, more preferably 2.3 or lower, still more preferably 2.0 or lower, yet more preferably 1.5 or lower.

<19>

The hair cosmetic composition as described in any one of <1> to <18> above, which is preferably a one-agent type hair cosmetic composition.

<20>

The hair cosmetic composition as described in <19> above, which has a pH of preferably 4.0 or lower, more preferably 3.0 or lower, still more preferably 2.5 or lower, yet more preferably 2.0 or lower, and preferably 1.0 or higher, more preferably 1.2 or higher, still more preferably 1.5 or higher.

<23>

The hair cosmetic composition as described in any one of <1> to <18> above, which is a multi-agent type composition comprising a first agent containing components (B) and (D), and a second agent containing components (A) and (D), wherein component (C) is contained in the first agent and/or the second agent.

<24>

The hair cosmetic composition as described in <23> above, wherein the first agent preferably has a pH of 6.0 or lower, more preferably 5.0 or lower, still more preferably 4.5 or lower, and preferably 2.5 or higher, more preferably 3.0 or higher, still more preferably 3.5 or higher.

<25>

The hair cosmetic composition as described in <23> or <24> above, wherein the second agent preferably has a pH of 4.0 or lower, more preferably 3.0 or lower, still more preferably 2.5 or lower, yet more preferably 2.0 or lower, and preferably 1.0 or higher, more preferably 1.2 or higher, still more preferably 1.5 or higher.

<26>

The hair cosmetic composition as described in any one of <1> to <25> above, wherein one or more compositions forming the hair cosmetic composition contain one or more species selected from the group consisting of a cationic surfactant, a silicone, and a cationic polymer.

<27>

A method for the treatment of hair, realizing semi-permanent or permanent deforming of hair, the method comprising the following steps (i) and (ii);

(i) a step of applying the hair cosmetic composition as recited in any one of <19> to <22> to hair; and (ii) a step of heating and shaping the hair to which the hair cosmetic composition is applied.

<28>

The hair treatment method as described in <27>, the method comprising the following steps;

1) optionally wetting hair with water;

2) applying the hair cosmetic composition as recited any one of <19> to <22> to hair;

3) optionally allowing the hair to which the hair cosmetic composition has been applied to stand for 1 minute or more and 1 hour or less, wherein the hair may optionally be heated at 40° C. or higher and 90° C. or lower;

4) heating and shaping the hair at 50° C. or higher and 250° C. or lower;

5) optionally rinsing the hair;

6) optionally heating and reshaping the hair at 40° C. or higher and 230° C. or lower; and 7) optionally heating and further shaping the re-deformed hair at 40° C. or higher and 230° C. or lower.

<29>

A method for the treatment of hair, realizing semi-permanent or permanent deforming of hair, the method comprising the following steps (i) and (ii);

(i) a step of mixing the first agent and the second agent of the hair cosmetic composition as recited in any one of <23> to <26> and applying the obtained hair cosmetic composition to hair; and (ii) a step of heating and shaping the hair to which the hair cosmetic composition is applied.

<30>

The hair treatment method as described in <29>, the method comprising the following steps;

1) optionally wetting hair with water;

2) mixing the first agent and the second agent of the hair cosmetic composition as recited in any one of <23> to <26> and applying the obtained hair cosmetic composition to the hair;

3) optionally allowing the hair to which the hair cosmetic composition has been applied to stand for 1 minute or more and 1 hour or less, wherein the hair may optionally be heated at 40° C. or higher and 90° C. or lower;

4) heating and shaping the hair at 50° C. or higher and 250° C. or lower;

5) optionally rinsing the hair;

6) optionally heating and reshaping the hair at 40° C. or higher and 230° C. or lower; and 7) optionally heating and further shaping the re-deformed hair at 40° C. or higher and 230° C. or lower.

<31>

A method for the treatment of hair, realizing semi-permanent or permanent deforming of hair, the method comprising the following steps (i) and (ii);

(i) a step of applying the first agent of the multi-agent type hair cosmetic composition as recited in any one of <23> to <26> to hair and then applying the second agent of the composition as recited in any one of <23> to <26> to a portion of the hair to which the first agent has been applied; and (ii) a step of heating and shaping the hair to which the hair cosmetic composition is applied.

<32>

The hair treatment method as described in <31>, the method comprising the following steps;

1) optionally wetting hair with water;

2) applying, to the hair, the first agent of the multi-agent type hair cosmetic composition as recited in any one of <23> to <26>;

3) optionally allowing the hair to which the first agent has been applied to stand for 1 minute or more and 1 hour or less, wherein the hair may optionally be heated at 40° C. or higher and 90° C. or lower;

4) optionally rinsing the first agent applied onto the hair;

5) applying, to a portion of the hair to which the first agent has been applied, the second agent of the multi-agent type hair cosmetic composition as recited in any one of <23> to <26>;

6) optionally allowing the hair to which the second agent has been applied to stand for 1 minute or more and 1 hour or less, wherein the hair may optionally be heated at 40° C. or higher and 90° C. or lower;

7) heating and shaping the hair at 50° C. or higher and 250° C. or lower;

8) optionally rinsing the hair;

9) optionally heating and reshaping the hair at 40° C. or higher and 230° C. or lower; and 10) optionally heating and further shaping the re-deformed hair at 40° C. or higher and 230° C. or lower.

<33>

The hair treatment method as described in any one of <27> to <32>, wherein the step of heating and shaping the hair is preferably performed under the conditions where evaporation of water is suppressed.

<34>

The hair treatment method as described in any one of <27> to <33>, which method preferably includes no step of applying, to the hair, a hair treatment agent containing a reducing agent.

<35>

The hair treatment method as described in any one of <27> to <34>, which method preferably includes no step of applying, to the hair, a strongly alkaline hair treatment agent having a pH of 12 or higher and 14 or lower.

<36>

A hair cosmetic composition, which is a one-agent type hair cosmetic composition composed of a single agent, or a multi-agent type hair cosmetic composition composed of multiple agents, wherein the hair cosmetic composition totally comprising the following components (A) to (D):

(A): 2.5 mass % or higher and 25 mass % or lower of one or more compound(s) selected from the group consisting of glyoxylic acid, glyoxylic acid hydrate, glyoxylate salt and glyoxylamide, (B1): 5 mass % or higher and 40 mass % or lower of resorcin, (C): 0.1 mass % or higher and 10 mass % or lower of one or more compound(s) selected from the group consisting of benzyl alcohol, phenoxyethanol, 1,2-butanediol, dipropylene glycol, glycerin, PEG-8, PPG-9, propylene glycol and ethylhexyl glycerin, and (D): water;

wherein the molar ratio of component (B1) to component (A), (B1)/(A), is 0.5 or higher and 1.7 or lower, wherein the pH of the hair cosmetic composition is 1.0 or higher and 3.0 or lower in the case where the hair cosmetic composition is the one-agent type composition, and wherein the pH of the first agent containing the component (B1) is 2.5 or higher and 5.0 or lower in the case where the hair cosmetic composition is the multi-agent type composition.

<37>

A hair treatment method for semi-permanently or permanently deforming hair shape, the method comprising the following steps (i) and (ii):

(i) a step of applying a hair cosmetic composition; and (ii) a step of heating and shaping the hair to which the hair cosmetic composition is applied;

wherein the hair cosmetic composition is a one-agent type hair cosmetic composition composed of a single agent, or a multi-agent type hair cosmetic composition composed of multiple agents, wherein the hair cosmetic composition totally comprising the following components (A) to (D):

(A): 2.5 mass % or higher and 25 mass % or lower of one or more compound(s) selected from the group consisting of glyoxylic acid, glyoxylic acid hydrate, glyoxylate salt and glyoxylamide, (B1): 5 mass % or higher and 40 mass % or lower of resorcin, (C): 0.1 mass % or higher and 10 mass % or lower of one or more compound(s) selected from the group consisting of benzyl alcohol, phenoxyethanol, 1,2-butanediol, dipropylene glycol, glycerin, PEG-8, PPG-9, propylene glycol and ethylhexyl glycerin, and (D): water;

wherein the molar ratio of component (B1) to component (A), (B1)/(A), is 0.5 or higher and 1.7 or lower, wherein the pH of the hair cosmetic composition is 1.0 or higher and 3.0 or lower in the case where the hair cosmetic composition is the one-agent type composition, and wherein the pH of the first agent containing the component (B1) is 2.5 or higher and 5.0 or lower in the case where the hair cosmetic composition is the multi-agent type composition.

<38>

A hair cosmetic composition, which is a one-agent type hair cosmetic composition composed of a single agent, or a multi-agent type hair cosmetic composition composed of multiple agents, wherein the hair cosmetic composition totally comprising the following components (A) to (D):

(A): 2.5 mass % or higher and 25 mass % or lower of one or more compound(s) selected from the group consisting of glyoxylic acid, glyoxylic acid hydrate, glyoxylate salt and glyoxylamide, (B2): 5 mass % or higher and 30 mass % or lower of one or more phenolic compound(s) selected from the group consisting of 2-methylresorcin, 4-butylresorcin (trivial name: Rucinol), 4-hexylresorcin, 4-(1-phenylethyl)resorcin (trivial name: Symwhite377), 4-chlororesorcin, 5-(hydroxyphenylethenyl)resorcin (trivial name: resveratrol), 5-(hydroxyphenylethenyl)-1,3-dimethoxybenzene (trivial name: Pterostilbene), 3-hydroxyphenyl-1-(benzene-2,4,6-triol)propane-1-on (trivial name: Phloretin), 4-(2,4-dihydroxybenzoyl)resorcin (trivial name: Benzophenone-2) and 1-naphthol, (C): 0.1 mass % or higher and 10 mass % or lower of one or more compound(s) selected from the group consisting of benzyl alcohol, phenoxyethanol, 1,2-butanediol, dipropylene glycol, glycerin, PEG-8, PPG-9, propylene glycol and ethylhexyl glycerin, and (D): water;

wherein the molar ratio of component (B2) to component (A), (B2)/(A), is 0.1 or higher and 2.0 or lower, wherein the pH of the hair cosmetic composition is 1.0 or higher and 3.0 or lower in the case where the hair cosmetic composition is the one-agent type composition, and wherein the pH of the first agent containing the component (B2) is 2.5 or higher and 5.0 or lower in the case where the hair cosmetic composition is the multi-agent type composition.

<39>

A hair treatment method for semi-permanently or permanently deforming hair shape, the method comprising the following steps (i) and (ii):

(i) a step of applying a hair cosmetic composition; and (ii) a step of heating and shaping the hair to which the hair cosmetic composition is applied;

wherein the hair cosmetic composition is a one-agent type hair cosmetic composition composed of a single agent, or a multi-agent type hair cosmetic composition composed of multiple agents, wherein the hair cosmetic composition totally comprising the following components (A) to (D):

(A): 2.5 mass % or higher and 25 mass % or lower of one or more compound(s) selected from the group consisting of glyoxylic acid, glyoxylic acid hydrate, glyoxylate salt and glyoxylamide, (B2): 5 mass % or higher and 30 mass % or lower of one or more phenolic compound(s) selected from the group consisting of 2-methylresorcin, 4-butylresorcin (trivial name: Rucinol), 4-hexylresorcin, 4-(1-phenylethyl)resorcin (trivial name: Symwhite377), 4-chlororesorcin, 5-(hydroxyphenylethenyl)resorcin (trivial name: resveratrol), 5-(hydroxyphenylethenyl)-1,3-dimethoxybenzene (trivial name: Pterostilbene), 3-hydroxyphenyl-1-(benzene-2,4,6-triol)propane-1-on (trivial name: Phloretin), 4-(2,4-dihydroxybenzoyl)resorcin (trivial name: Benzophenone-2) and 1-naphthol, (C): 0.1 mass % or higher and 10 mass % or lower of one or more compound(s) selected from the group consisting of benzyl alcohol, phenoxyethanol, 1,2-butanediol, dipropylene glycol, glycerin, PEG-8, PPG-9, propylene glycol and ethylhexyl glycerin, and (D): water;

wherein the molar ratio of component (B2) to component (A), (B2)/(A), is 0.1 or higher and 2.0 or lower, wherein the pH of the hair cosmetic composition is 1.0 or higher and 3.0 or lower in the case where the hair cosmetic composition is the one-agent type composition, and wherein the pH of the first agent containing the component (B2) is 2.5 or higher and 5.0 or lower in the case where the hair cosmetic composition is the multi-agent type composition.

<40>

A hair cosmetic composition, which is a one-agent type hair cosmetic composition composed of a single agent, or a multi-agent type hair cosmetic composition composed of multiple agents, wherein the hair cosmetic composition totally comprising the following components (A) to (D):

(A): 2.5 mass % or higher and 25 mass % or lower of one or more compound(s) selected from the group consisting of glyoxylic acid, glyoxylic acid hydrate, glyoxylate salt and glyoxylamide, (B3): 5 mass % or higher and 30 mass % or lower of one or more phenolic compound(s) selected from the group consisting of catechin, epigallocatechin, epigallocatechin gallate, naringenin and equol, (C): 0.1 mass % or higher and 10 mass % or lower of one or more compound(s) selected from the group consisting of benzyl alcohol, phenoxyethanol, 1,2-butanediol, dipropylene glycol, glycerin, PEG-8, PPG-9, propylene glycol and ethylhexyl glycerin, and (D): water;

wherein the molar ratio of component (B3) to component (A), (B3)/(A), is 0.1 or higher and 2.0 or lower, wherein the pH of the hair cosmetic composition is 1.0 or higher and 3.0 or lower in the case where the hair cosmetic composition is the one-agent type composition, and wherein the pH of the first agent containing the component (B3) is 2.5 or higher and 5.0 or lower in the case where the hair cosmetic composition is the multi-agent type composition.

<41>
A hair treatment method for semi-permanently or permanently deforming hair shape, the method comprising the following steps (i) and (ii):

(i) a step of applying a hair cosmetic composition; and
(ii) a step of heating and shaping the hair to which the hair cosmetic composition is applied;

wherein the hair cosmetic composition is a one-agent type hair cosmetic composition composed of a single agent, or a multi-agent type hair cosmetic composition composed of multiple agents, wherein the hair cosmetic composition totally comprising the following components (A) to (D):

(A): 2.5 mass % or higher and 25 mass % or lower of one or more compound(s) selected from the group consisting of glyoxylic acid, glyoxylic acid hydrate, glyoxylate salt and glyoxylamide, (B3): 5 mass % or higher and 30 mass % or lower of one or more phenolic compound(s) selected from the group consisting of catechin, epigallocatechin, epigallocatechin gallate, naringenin and equol, (C): 0.1 mass % or higher and 10 mass % or lower of one or more compound(s) selected from the group consisting of benzyl alcohol, phenoxyethanol, 1,2-butanediol, dipropylene glycol, glycerin, PEG-8, PPG-9, propylene glycol and ethylhexyl glycerin, and (D): water;

wherein the molar ratio of component (B3) to component (A), (B3)/(A), is 0.1 or higher and 2.0 or lower, wherein the pH of the hair cosmetic composition is 1.0 or higher and 3.0 or lower in the case where the hair cosmetic composition is the one-agent type composition, and wherein the pH of the first agent containing the component (B3) is 2.5 or higher and 5.0 or lower in the case where the hair cosmetic composition is the multi-agent type composition.

<42>
The hair cosmetic composition as described in <36>, <38> or <40>, wherein the amount of precursor is preferably 0.1 mass % or lower, more preferably the composition contains substantially no precursor.

<43>
The hair treatment method as described in <37>, <39> or <41>, wherein the amount of precursor in the hair cosmetic composition is preferably 0.1 mass % or lower, more preferably the composition contains substantially no precursor.

<44>
The hair cosmetic composition as described in <36>, <38> or <40>, wherein the amount of boric acid and silicic acid is preferably 0.1 mass % or lower, more preferably the composition contains substantially no boric acid and silicic acid.

<45>
The hair treatment method as described in <37>, <39> or <41>, wherein the amount of boric acid and silicic acid in the hair cosmetic composition is preferably 0.1 mass % or lower, more preferably the composition contains substantially no boric acid and silicic acid.

<46>
The hair cosmetic composition as described in <36>, <38> or <40>, wherein the amount of hair reducing agent is preferably 0.1 mass % or lower, more preferably the composition contains substantially no hair reducing agent.

<47>
The hair treatment method as described in <37>, <39> or <41>, wherein the amount of hair reducing agent in the hair cosmetic composition is preferably 0.1 mass % or lower, more preferably the composition contains substantially no hair reducing agent.

<48>
Use of a hair cosmetic composition, which is a one-agent type hair cosmetic composition composed of a single agent, or a multi-agent type hair cosmetic composition composed of multiple agent, and which totally comprises the following components (A) to (D):

(A): one or more compounds selected from the group consisting of glyoxylic acid, a glyoxylic acid hydrate, a glyoxylate salt, and a glyoxylamide;

(B): a phenolic compound having an electron-donating group on at least one m-position, preferably two or three positions, and having a hydrogen atom on at least one of the o-positions and the p-position, wherein the electron-donating group on the m-position may form, together with an adjacent carbon atom, a benzene ring optionally substituted with hydroxyl group(s);

(C): organic solvent having a boiling point of 100° C. or higher at 1,013.25 hPa; and (D): water, wherein the component (C) content, relative to the total composition of the hair cosmetic composition, is 0.1 mass % or higher and 20 mass % or lower, for semi-permanently or permanently deforming the shape of hair.

EXAMPLES

Example 1 and Comparative Example 1

Hair cosmetic compositions shown in Table 1 were prepared. Shape-giving effect, handling performance and touch feeling were evaluated through the following procedures and on the basis of the following criteria. The results are also shown in Table 1. The pH of each composition was obtained from a sample of the composition which was not diluted after preparation and was measured at room temperature (25° C.) by means of a pH meter (model F-52, product of HORIBA).

<Semi-Permanent Curling (Shape-Giving Effect)>

1. A 25-cm tress of Caucasian straight hair (untreated) (0.5 g) was wetted with tap water at 30° C. for 30 seconds, and the wetted hair tress was wound around a plastic rod (diameter: 14 mm), followed by fixing with a clip.

2. Onto the thus-wound hair tress, each hair cosmetic composition (1 g) was applied, and the hair tress wound over the rod was tightly wrapped by a plastic film. The sample was heated in an oven at 90° C. for 1 hour.

3. The tress was removed from the oven, and cooled to a room temperature.

4. The tress was removed from the rod, and was then rinsed with running tap water at 30° C. for 30 seconds. Thereafter, a shampoo for assessment was lathered on the tress for 60 seconds.

5. The tress was rinsed with running tap water at 30° C. for 30 seconds, and immersed at an infinite bath ratio in tap water at 30° C. for 60 seconds. Thereafter, the tress was gently pulled up out of the water while holding the root thereof, and water was then drained off by lightly shaking it.

6. The hair tress sample was allowed to stand in a laboratory for 2 hours, while the sample was suspended, and dried, followed by combing. Thereafter, the length of the hair tress sample perpendicularly suspended (i.e., the distance from the root of the sample to a point most distant therefrom) was measured.

(Evaluation Criteria of Shape-Giving Effect by Component (C))

The percent decrease in tress length (I, %), obtained from the length of the untreated tress sample ($L_0$) and the length of the treated tress sample (L) by the following equation:

$$I=[(L_0-L)/L_0]\times 100$$

was defined as the curl tightness.

The percent decrease in tress length ($I_0$), which was obtained from a hair cosmetic composition sample (Comparative Example 1) free of component (C), was employed as a standard. The percent decrease in tress length ($I_c$), which was obtained from a hair cosmetic composition sample (Example 1) containing component (C) was determined, and the relative percentage (%) was determined by the following equation:

Relative shape-giving effect relative to the case of no component(C) (%)=($I_c/I_0$)×100.

(Basis of Sensory Assessment of Shape-Giving Effect by Component (C))

The curl tightness of the treated tress was visually evaluated on the basis of the following criteria.
5: Even stronger shape-giving effect
4: Stronger shape-giving effect
3: Adequate shape-giving effect
2: Inadequate shape-giving effect
1: No shape-giving effect <Touch Feeling after Treatment>

Touch feeling of a hair tress sample was evaluated by a hair tress sample immediately after <Semi-permanent curling (shape-giving effect)> and evaluated on the basis of the suppleness of hair during touch with the hand(s).

(Evaluation Criteria)
5: Very soft touch feeling as compared with untreated hair
4: Soft touch feeling as compared with untreated hair
3: Same touch feeling as that of untreated hair
2: Stiff touch feeling as compared with untreated hair
1: Very stiff touch feeling as compared with untreated hair

| (Formulation of shampoo for assessment) | |
|---|---|
| Components | (mass %) |
| Sodium laureth sulfate | 15.5 |
| Lauramide DEA | 1.5 |
| Sodium benzoate | 0.5 |
| EDTA-2Na | 0.3 |
| Phosphoric acid | amount to pH 7 |
| Deionized water | balance |
| Total | 100 |

TABLE 1

| | | | (mass %) | |
|---|---|---|---|---|
| | | | Example 1 | Comparative Example 1 |
| Formulation [mass %] | (B) | Resorcin | 30 | 30 |
| | (A) | Glyoxylic acid | 20 | 20 |
| | (C) | Benzyl alcohol | 2 | — |
| | — | Sodium hydroxide | * | * |
| | (D) | Purified water | bal | bal |
| | | Total | 100 | 100 |
| | | pH | 2.0 | 2.0 |
| Ratio of components | | Molar ratio (B)/(A) | 1.0 | 1.0 |
| | | Mass ratio (C)/[(A) + (B)] | 0.04 | 0 |
| Hair deforming | | Relative shape-giving effect (%) vs. Comp. Ex. 1 | 113.0 | standard |
| | | Sensory assessment | 5 | 5 |
| Touch feeling | | Touch feeling after drying | 4 | 2 |

* Amount for adjusting pH

Examples 2 to 7 and Comparative Examples 2 to 5

Two-agent type hair cosmetic compositions shown in Tables 2 and 3 were prepared. Shape-giving effect, touch feeling, and physical properties were evaluated through the following procedures and on the basis of the following criteria. The results are also shown in Tables 2 and 3.

<Semi-Permanent Curling (Shape-Giving Effect)>

1. A 25-cm tress of Caucasian straight hair (untreated) (0.5 g) was wetted with tap water at 30° C. for 30 seconds, and the wetted hair tress was wound around a plastic rod (diameter: 14 mm), followed by fixing with a clip.

2. Onto the thus-wound hair tress, a first agent formulation (1 g) was applied, and the hair tress wound over the rod was tightly wrapped by a plastic film. The sample was heated in an oven at 90° C. for 1 hour.

3. The tress was removed from the oven, and cooled to a room temperature.

4. The tress was removed from the rod, and was then rinsed with running tap water at 30° C. for 30 seconds. Thereafter, a shampoo for assessment was lathered on the tress for 60 seconds, and was then rinsed with running tap water at 30° C. for 30 seconds.

5. The wet hair tress was wound around a plastic rod (diameter: 14 mm) and fixed with a clip.

6. Onto the thus-wound hair tress, a second agent formulation (1 g) was applied, and the hair tress wound over the rod was tightly wrapped by a plastic film. The sample was heated in an oven at 90° C. for 1 hour.

7. The hair tress sample was removed from the oven and cooled to room temperature.

8. The hair tress sample was released from the rod and rinsed with a flow of tap water at 30° C. for 30 seconds. Then, a shampoo for assessment was lathered on the tress for 60 seconds.

9. The tress was rinsed with running tap water at 30° C. for 30 seconds, and immersed at an infinite bath ratio in tap water at 30° C. for 60 seconds. Thereafter, the tress was gently pulled up out of the water while holding the root thereof, and water was then drained off by lightly shaking it.

10. The hair tress sample was allowed to stand in a laboratory for 2 hours, while the sample was suspended, and dried, followed by combing. Thereafter, the length of the hair tress sample perpendicularly suspended (i.e., the distance from the root of the sample to a point most distant therefrom) was measured.

Notably, the aforementioned shampoo for assessment was also used.

The percent decrease in tress length (I, %), obtained from the length of the untreated tress sample ($L_0$) and the length of the treated tress sample (L) by the following equation:

$$I=[(L_0-L)/L_0]\times 100$$

was defined as the curl tightness.

The percent decrease in tress length ($I_0$), which was obtained from a hair cosmetic composition sample free of component (C), was employed as a standard. The percent decrease in tress length ($I_c$), which was obtained from a hair cosmetic composition sample containing component (C) was determined, and the relative percentage (%) was determined by the following equation. In Table 2, the relative shape-giving effect was calculated by using the percent decrease in tress length of Comparative Example 2 as $I_0$. In Table 3, the relative shape-giving effect was calculated by using the percent decrease in tress length of Comparative Example 5 as $I_0$.

Relative shape-giving effect relative to the case of no component(C) (%)=($I_c/I_0$)×100.

(Basis of Sensory Assessment of Shape-Giving Effect by Component (C))

The curl tightness of the treated tress was visually evaluated on the basis of the following criteria.
5: Even stronger shape-giving effect
4: Stronger shape-giving effect
3: Adequate shape-giving effect
2: Inadequate shape-giving effect
1: No shape-giving effect <Touch Feeling after Treatment>

Touch feeling of a hair tress sample was evaluated by a hair tress sample immediately after <Semi-permanent curling (shape-giving effect)> and evaluated on the basis of the suppleness of hair during touch with the hand(s).

(Evaluation Criteria)
5: Very soft touch feeling as compared with untreated hair
4: Soft touch feeling as compared with untreated hair
3: Same touch feeling as that of untreated hair
2: Stiff touch feeling as compared with untreated hair
1: Very stiff touch feeling as compared with untreated hair <Bending Modulus of Dry Hair>

Measurement of the bending modulus of treated dry hair was carried out for Examples 2 to 4, Comparative Example 2, and Reference Example shown in Table 2.

The test was performed by the following procedure.

1. Twenty (20) fibers of hair were sampled by cutting the root of dried hair after treatment. A 5-mm hair fiber fragment was taken from an intermediate portion of each hair fiber between the root and end thereof, whereby 20 5-mm hair fiber fragments were obtained in total. The hair fiber fragment was placed in a room (20° C., 60% RH) for 24 hours for humidity adjustment.

2. The hair fiber fragments (dried state) were set to a fiber/hair bending test system FBS 900 (product of DIA-STRON limited) and were subjected to automatic measurement. The bending modulus were obtained from the average of the measured values (N=20).

In addition, the change of bending modulus using the hair cosmetic composition containing the component (C), relative to the hair cosmetic composition not containing the component (C) (comparative example 2) was measured.

Higher bending modulus indicates stiffer hair, while lower bending modulus indicates softer hair.

TABLE 2

| | | | (mass %) | Examples | | | | Comparative Examples | | | Ref. |
|---|---|---|---|---|---|---|---|---|---|---|---|
| | | | | 2 | 3 | 4 | 5 | 2 | 3 | 4 | |
| First agent | Formulation [mass %] | (B) | 4-Phenylethylresorcin | 20 | 20 | 20 | 20 | 20 | 20 | 20 | Untreated hair |
| | | (C) | Glycerin | 2 | — | — | — | — | 20 | — | |
| | | | PEG-8 | — | 2 | — | — | — | — | 20 | |
| | | | Benzyl alcohol | — | — | 2 | 5 | — | — | — | |
| | | — | Ethanol | 40 | 40 | 40 | 40 | 40 | 40 | 40 | |
| | | | Sodium hydroxide | * | * | * | * | * | * | * | |
| | | (D) | Purified water | bal | bal | bal | bal | bal | bal | bal | |
| | | | Total | 100 | 100 | 100 | 100 | 100 | 100 | 100 | |
| | | | pH | 4.0 | 4.0 | 4.0 | 4.0 | 4.0 | 4.0 | 4.0 | |
| Second agent | Formulation [mass %] | (A) | Glyoxylic acid | 20 | 20 | 20 | 20 | 20 | 20 | 20 | |
| | | (C) | Glycerin | 2 | — | — | — | — | 20 | — | |
| | | | PEG-8 | — | 2 | — | — | — | — | 20 | |
| | | | Benzyl alcohol | — | — | 2 | — | — | — | — | |
| | | — | Sodium hydroxide | * | * | * | * | * | * | * | |
| | | (D) | Purified water | bal | bal | bal | bal | bal | bal | bal | |
| | | | Total | 100 | 100 | 100 | 100 | 100 | 100 | 100 | |
| | | | pH | 2.0 | 2.0 | 2.0 | 2.0 | 2.0 | 2.0 | 2.0 | |
| Ratio of components | | | Molar ratio (B)/(A) | 0.34 | 0.34 | 0.34 | 0.34 | 0.34 | 0.34 | 0.34 | |
| | | | Mass ratio (C)/[(A) + (B)] | 0.10 | 0.10 | 0.10 | 0.125 | 0.00 | 1.00 | 1.00 | |
| Shape-giving | | | Relative shape-giving effect (%) vs. Comp. Ex. 2 | 88 | 73 | 73 | 81 | standard | 47 | 18 | |
| | | | Sensory assessment | 4 | 4 | 4 | 4 | 5 | 2 | 2 | |

TABLE 2-continued

|  | (mass %) | Examples | | | | Comparative Examples | | | Ref. |
|---|---|---|---|---|---|---|---|---|---|
|  |  | 2 | 3 | 4 | 5 | 2 | 3 | 4 |  |
| Touch feeling | Touch feeling after drying | 4 | 4 | 4 | 4 | 2 | 5 | 5 |  |
| Physical properties | Bending modulus after drying [GPa] | 6.09 | 5.88 | 5.77 |  | 6.19 |  |  | 5.51 |
|  | Change in bending modulus by component (C) [GPa] | −0.1 | −0.31 | −0.42 |  | 0 |  |  | −0.68 |

*: Amount for adjusting pH

TABLE 3

|  |  |  |  | Examples | | Comparative Examples |
|---|---|---|---|---|---|---|
|  |  | (mass %) |  | 6 | 7 | 5 |
| First agent | Formulation [mass %] | (B) | (+)-Catechin | 20 | 20 | 20 |
|  |  | (C) | Benzyl alcohol | 2 | 5 | — |
|  |  | — | Ethanol | 40 | 40 | 40 |
|  |  |  | Sodium hydroxide | * | * | * |
|  |  | (D) | Purified water | bal | bal | bal |
|  |  |  | Total | 100 | 100 | 100 |
|  |  | pH |  | 4.0 | 4.0 | 4.0 |
| Second agent | Formulation [mass %] | (A) | Glyoxylic acid | 20 | 20 | 20 |
|  |  | (C) | Benzyl alcohol | 2 | — | — |
|  |  | — | Sodium hydroxide | * | * | * |
|  |  | (D) | Purified water | bal | bal | bal |
|  |  |  | Total | 100 | 100 | 100 |
|  |  | pH |  | 2.0 | 2.0 | 2.0 |
| Ratio of components |  | Molar ratio (B)/(A) |  | 0.25 | 0.25 | 0.25 |
|  |  | Mass ratio (C)/[(A) + (B)] |  | 0.10 | 0.125 | 0.00 |
| Shape-giving |  | Relative effect for deforming the shape of hair (%) vs. Comp. Ex. 5 |  | 97 | 89 | standard |
|  |  | Sensory assessment |  | 5 | 4 | 5 |
| Touch feeling |  | Touch feeling after drying |  | 4 | 4 | 2 |

*: Amount for adjusting pH

The invention claimed is:
1. A hair cosmetic composition, which is a one-agent type hair cosmetic composition composed of a single agent, totally comprising the following components (A) to (D), the component (C) content, relative to the total composition of the hair cosmetic composition, being 0.1 mass % or higher and lower than 20 mass %:
(A): one or more compounds selected from the group consisting of glyoxylic acid, a glyoxylic acid hydrate, a glyoxylate salt, and a glyoxylamide;
(B): one or more phenolic compounds selected from component (B1), (B2) and (B3):
(B1): resorcin;
(B2): a compound of formula (1) as defined below;
(B3): a compound of formula (2) as defined below;
(C): organic solvent having a boiling point of 100° C. or higher at 1,013.25 hPa; and
(D): water:

Formula (1)

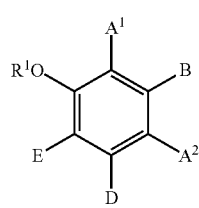

wherein:
$R^1$ represents a hydrogen atom or a methyl group;
$A^1$ and $A^2$, which may be identical to or different from each other, each represent a hydrogen atom, a C1 to C12 linear-chain or branched-chain alkyl or alkenyl group, an optionally substituted C7 to C12 aralkyl or arylalkenyl group, a C1 to C6 linear-chain or branched-chain alkoxy or alkenyloxy group, a halogen atom, or —CO—$R^2$ (wherein $R^2$ represents a C1 to C12 linear-chain or branched-chain alkyl or alkenyl group, an optionally substituted C7 to C12 aralkyl or arylalkenyl group, or an optionally substituted C6 to C12 aromatic hydrocarbon group);
B represents a hydrogen atom, a C1 to C12 linear-chain or branched-chain alkyl or alkenyl group, an optionally substituted C7 to C12 aralkyl or arylalkenyl group, or —$OR^3$ or —$COOR^3$ (wherein $R^3$ represents a hydrogen atom or a C1 to C6 linear-chain or branched-chain alkyl or alkenyl group);
D represents a hydrogen atom, a hydroxyl group, a methyl group, or a C1 to C12 linear-chain or branched-chain alkoxy or alkenyloxy group; and
E represents a hydrogen atom, a hydroxyl group, a C1 to C6 linear-chain or branched-chain alkyl or alkenyl group, or a C1 to C6 linear-chain or branched-chain alkoxy or alkenyloxy group,
wherein two or three of $A^1$, $A^2$, B, and E each are a hydrogen atom, with each of remaining being a group which is not a sulfo group, and in the case where D is a hydrogen atom or a methyl group, $A^1$ and B, or $A^2$ and B form an optionally hydroxyl group-substituted benzene ring with two adjacent carbon atoms;

Formula (2)

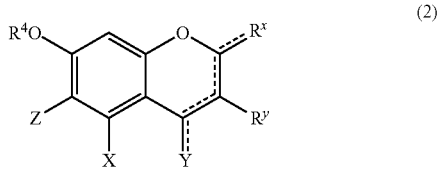

wherein,
- $R^4$ represents a hydrogen atom or a methyl group;
- X represents a hydrogen atom, a hydroxyl group, or a methoxy group;
- Y represents a hydrogen atom, an oxygen atom, a hydroxyl group, or a methoxy group;
- Z represents a hydrogen atom or a C1 to C5 linear-chain or branched-chain alkyl or alkenyl group;
- $R^x$ represents a hydrogen atom, an oxygen atom, a hydroxy group, a methoxy group, or an aromatic hydrocarbon group, which is optionally substituted with up to three hydroxy groups or methoxy groups and which optionally forms a condensed ring with 1,3-dioxolane,
- $R^y$ represents a hydrogen atom, a hydroxy group, a methoxy group, or an aromatic hydrocarbon group, which is optionally substituted with up to three hydroxy groups or methoxy groups and which optionally forms a condensed ring with 1,3-dioxolane, or an arylcarbonyloxy group or aralkylcarbonyloxy group, which is optionally substituted with up to three hydroxy groups or methoxy groups,
- a dotted line portion may be a double bond;
- each of the combinations of the dotted line and the solid line being adjacent to $R^x$ or Y denotes a double bond in the case where $R^x$ or Y is an oxygen atom, and denotes a single bond in the other cases; and
- Z represents a C1 to C5 linear-chain or branched-chain alkyl or alkenyl group, only when $R^x$ or $R^y$ is an o,p-dihydroxyaromatic hydrocarbon group, and represents a hydrogen atom in the other cases.

2. The hair cosmetic composition according to claim 1, wherein component (C) is an organic solvent whose Log P is less than 10.

3. The hair cosmetic composition according to claim 1, wherein the molar ratio of component (B) to component (A), (B)/(A), of the hair cosmetic composition applied to hair is 0.001 or higher and lower than 2.5.

4. The hair cosmetic composition according to claim 1, which has a component (A) content, relative to the total composition of the hair cosmetic composition and in terms of glyoxylic acid, of 1 mass % or higher and 30 mass % or lower.

5. The hair cosmetic composition according to claim 1, which has a component (B) content, relative to the total composition of the hair cosmetic composition of 0.2 mass % of higher to 40 mass % or lower.

6. The hair cosmetic composition according to claim 1, wherein the glyoxylamide of component (A) is N-glyoxyloylcarbocysteine or N-glyoxyloylkeratinamino acid.

7. The hair cosmetic composition according to claim 1, wherein component (B) is component (B2).

8. The hair cosmetic composition according to claim 1, wherein component (B) is component (B3).

9. The hair cosmetic composition according to claim 1, wherein component (B) is component (B1), which is resorcin.

10. The hair cosmetic composition according to claim 1, wherein component (C) is one or more compounds selected from following (c1) to (c5):

(c1) compounds represented by formula (3)

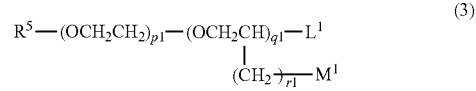

(wherein $R^5$ represents a group $R^6$-Ph-$R^7$— (wherein $R^6$ represents a hydrogen atom, a methyl group, or a methoxy group; $R^7$ represents a chemical bond or a C1 to C3 saturated or unsaturated divalent hydrocarbon group; and Ph represents a p-phenylene group); $L^1$ and $M^1$ each represent a hydrogen atom or a hydroxyl group; and each of $p^1$, $q^1$, and $r^1$ is an integer of 0 to 5, wherein, in the case of $p^1=q^1=0$, $L^1$ is a hydroxyl group, and $R^5$ is not a group $R^6$-Ph-);

(c2) compounds represented by formula (4)

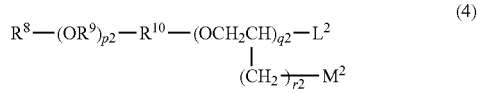

(wherein $R^8$ represents a hydrogen atom or a C1 to C12 linear-chain or branched-chain alkyl group; $R^9$ represents a C1 to C10 linear-chain or branched-chain saturated divalent hydrocarbon group optionally substituted with one hydroxyl group; $R^{10}$ represents a chemical bond or a C1 to C5 linear-chain or branched-chain divalent saturated hydrocarbon group optionally substituted with one $[CH_2CH(Q)O]_s$ (wherein Q represents a hydrogen atom or a methyl group, and s is an integer of 1 to 20); $L^2$ represents a hydrogen atom, a hydroxyl group, a C1 to C10 linear-chain or branched-chain alkoxy group or a phenoxy group; $M^2$ represents a hydrogen atom or a hydroxyl group; each of $p^2$ and $q^2$ is an integer of 0 to 20; and $r^2$ is an integer of 0 to 10);

(c3) N-alkyl- or N-alkenylpyrrolidones in which a C1 to C18 alkyl or alkenyl group is bonded to the nitrogen atom;

(c4) C3 or C4 alkylene carbonates optionally substituted with a hydroxyl group; and (c5) lactones or cyclic ketones represented by formula (5), (6), or (7)

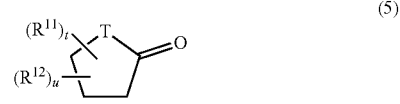

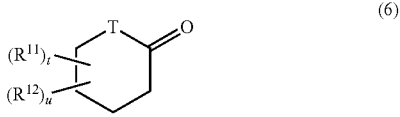

-continued

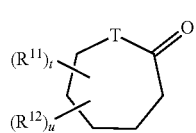
(7)

(wherein T represents a methylene group or an oxygen atom; $R^{11}$ and $R^{12}$ are substituents which are different from each other; and each of t and u is 0 or 1).

11. The hair cosmetic composition according to claim 1, wherein the total amount of component reducing hair protein, relative to the total hair cosmetic composition, is less than 0.1 mass %.

12. The hair cosmetic composition according to claim 1, which has a pH of 4.0 or lower.

13. A hair cosmetic composition, which is a multi-agent type hair cosmetic composition composed of multiple agents,
wherein the hair cosmetic composition totally comprising the following components (A) to (D), the component (C) content, relative to the total composition of the hair cosmetic composition, being 0.1 mass % or higher and lower than 20 mass %:
(A): one or more compounds selected from the group consisting of glyoxylic acid, a glyoxylic acid hydrate, a glyoxylate salt, and a glyoxylamide;
(B): one or more phenolic compounds selected from component (B1), (B2) and (B3):
    (B1): resorcin;
    (B2): a compound of formula (1) as defined below;
    (B3): a compound of formula (2) as defined below;
(C): organic solvent having a boiling point of 100° C. or higher at 1,013.25 hPa; and
(D): water:

Formula (1):

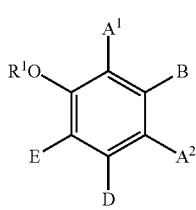
(1)

wherein:
$R^1$ represents a hydrogen atom or a methyl group;
$A^1$ and $A^2$, which may be identical to or different from each other, each represent a hydrogen atom, a C1 to C12 linear-chain or branched-chain alkyl or alkenyl group, an optionally substituted C7 to C12 aralkyl or arylalkenyl group, a C1 to C6 linear-chain or branched-chain alkoxy or alkenyloxy group, a halogen atom, or —CO—$R^2$ (wherein $R^2$ represents a C1 to C12 linear-chain or branched-chain alkyl or alkenyl group, an optionally substituted C7 to C12 aralkyl or arylalkenyl group, or an optionally substituted C6 to C12 aromatic hydrocarbon group);
B represents a hydrogen atom, a C1 to C12 linear-chain or branched-chain alkyl or alkenyl group, an optionally substituted C7 to C12 aralkyl or arylalkenyl group, or —O$R^3$ or —COO$R^3$ (wherein $R^3$ represents a hydrogen atom or a C1 to C6 linear-chain or branched-chain alkyl or alkenyl group);
D represents a hydrogen atom, a hydroxyl group, a methyl group, or a C1 to C12 linear-chain or branched-chain alkoxy or alkenyloxy group; and
E represents a hydrogen atom, a hydroxyl group, a C1 to C6 linear-chain or branched-chain alkyl or alkenyl group, or a C1 to C6 linear-chain or branched-chain alkoxy or alkenyloxy group,
wherein two or three of $A^1$, $A^2$, B, and E each are a hydrogen atom, with each of remaining being a group which is not a sulfo group, and in the case where D is a hydrogen atom or a methyl group, $A^1$ and B, or $A^2$ and B form an optionally hydroxyl group-substituted benzene ring with two adjacent carbon atoms;

Formula (2)

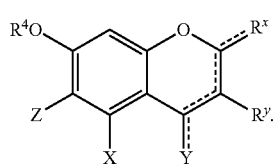
(2)

wherein,
$R^4$ represents a hydrogen atom or a methyl group;
X represents a hydrogen atom, a hydroxyl group, or a methoxy group;
Y represents a hydrogen atom, an oxygen atom, a hydroxyl group, or a methoxy group;
Z represents a hydrogen atom or a C1 to C5 linear-chain or branched-chain alkyl or alkenyl group;
$R^x$ represents a hydrogen atom, an oxygen atom, a hydroxy group, a methoxy group, or an aromatic hydrocarbon group, which is optionally substituted with up to three hydroxy groups or methoxy groups and which optionally forms a condensed ring with 1,3-dioxolane,
$R^y$ represents a hydrogen atom, a hydroxy group, a methoxy group, or an aromatic hydrocarbon group, which is optionally substituted with up to three hydroxy groups or methoxy groups and which optionally forms a condensed ring with 1,3-dioxolane, or an arylcarbonyloxy group or aralkylcarbonyloxy group, which is optionally substituted with up to three hydroxy groups or methoxy groups,
a dotted line portion may be a double bond;
each of the combinations of the dotted line and the solid line being adjacent to $R^x$ or Y denotes a double bond in the case where $R^x$ or Y is an oxygen atom, and denotes a single bond in the other cases; and
Z represents a C1 to C5 linear-chain or branched-chain alkyl or alkenyl group, only when $R^x$ or $R^y$ is an o,p-dihydroxyaromatic hydrocarbon group, and represents a hydrogen atom in the other cases, wherein the multi-agent type composition comprises a first agent containing components (B) and (D), and a second agent containing components (A) and (D), wherein component (C) is contained in the first agent and/or the second agent, wherein the first agent has a pH of 6.0 or lower.

14. The hair cosmetic composition according to claim 13, wherein the second agent has a pH of 4.0 or lower.

15. A hair treatment method for semi-permanently or permanently deforming the shape of hair, the method comprising the following steps (i) and (ii);
   (i) a step of applying the hair cosmetic composition as recited in claim 1 to hair; and
   (ii) a step of heating and shaping the hair to which the hair cosmetic composition is applied.

16. A hair treatment method for semi-permanently or permanently deforming the shape of hair, the method comprising the following steps (i) and (ii);
   (i) a step of mixing the first agent and the second agent of the hair cosmetic composition as recited in claim 13 and applying the obtained hair cosmetic composition to hair; and
   (ii) a step of heating and shaping the hair to which the hair cosmetic composition is applied.

17. A hair treatment method for semi-permanently or permanently deforming the shape of hair, the method comprising the following steps (i) and (ii);
   (i) a step of applying the first agent of the hair cosmetic composition as recited in claim 13 to hair and then applying the second agent of the composition as recited in claim 13 onto the portion of hair where the first agent was applied; and
   (ii) a step of heating and shaping the hair to which the hair cosmetic composition is applied.

18. The hair treatment method according to claim 17, comprising a step of rinsing the first agent in the step (i), after applying the first agent to the hair, and before applying the second agent onto the portion of hair where the first agent was applied.

19. The hair treatment method according to claim 18, comprising a step of allowing the hair to stand for 1 minute or more and 1 hour or less in the step (i), after applying the first agent to the hair, and before rinsing the first agent.

20. The hair treatment method according to claim 15 which method further includes, after step (i), a step of allowing the hair to stand to which the hair cosmetic composition has been applied, for 1 minute or more and 1 hour or less.

21. The hair treatment method according to claim 15, wherein the heating temperature in step (ii) is 50° C. or higher and 250° C. or lower.

22. The hair treatment method according to claim 15, wherein step (ii) is performed under the conditions where evaporation of water is suppressed.

23. The hair treatment method according to claim 15, which method includes no step of applying, to the hair, a hair cosmetic composition containing a reducing agent or a strongly alkaline hair treatment agent having a pH of 12 or higher and 14 or lower.

24. The hair treatment method according to claim 15, comprising a step of heating and re-deforming the shape of hair to different shape after the step (ii).

25. The hair cosmetic composition according to claim 10, wherein component (C) is (c1) and/or (c2).

* * * * *